United States Patent [19]

Doherty et al.

[11] Patent Number: 5,162,527
[45] Date of Patent: Nov. 10, 1992

[54] RENIN INHIBITORS, PROCESSES FOR PREPARING THEM, METHODS FOR USING THEM, AND COMPOSITIONS CONTAINING THEM

[75] Inventors: Annette M. Doherty, Ann Arbor; Harriet W. Hamilton, Chelsea; John C. Hodges, Ann Arbor; Joseph T. Repine, Ann Arbor; Ila Sircar, Ann Arbor, all of Mich.

[73] Assignee: Warner-Lambert Company, Morris Plains, N.J.

[21] Appl. No.: 676,047

[22] Filed: Mar. 27, 1991

Related U.S. Application Data

[60] Division of Ser. No. 384,236, Jul. 24, 1989, Pat. No. 5,063,207, which is a continuation-in-part of Ser. No. 206,023, Jun. 17, 1988, abandoned, which is a continuation-in-part of Ser. No. 113,772, Oct. 26, 1987, abandoned.

[51] Int. Cl.$^5$ .................. C07D 265/30; C07C 315/00
[52] U.S. Cl. .................. 544/159; 562/430; 548/542; 544/383
[58] Field of Search ............ 514/18, 19; 530/330, 530/331; 562/430; 544/106, 158, 159, 358, 383, 160; 548/542

[56] References Cited

PUBLICATIONS

Burger, "Medicinal Chemistry", Second edition, pp. 565–571, 573–581, 600–601 (1960).
Denkewalter et al., "Progress in Drug Research", vol. 10, pp. 510–512 (1966).
Bolis et al., "Renin Inhibitors. Dipeptide Analogues . . . " J. Med. Chem. 1987, 30, 1729–1737.
Haber et al., "Renin Inhibitors: A Search for Principles of Design", J. Card. Pharm., 10 (Suppl. 7):54–58, 1987.
Plattner et al., "Renin Inhibitors. Dipeptide Analogues . . . " J. Med Chem. 1988, 31, 2277–2288.

*Primary Examiner*—Merrell C. Cashion, Jr.
*Assistant Examiner*—B. Celsa
*Attorney, Agent, or Firm*—Elizabeth M. Anderson

[57] ABSTRACT

The invention concerns novel renin-inhibitory peptides which are useful for treating renin-associated hypertension, congestive heart failure, hyperaldosteronism and diseases caused by retroviruses including HTLV-I and -III. Processes for preparing the peptides, novel intermediates useful in the preparation thereof, compositions containing them, and methods of using them are included. Also included is a diagnostic method which uses the compounds to determine the presence of renin-associated hypertension, congestive heart failure, or hyperaldosteronism.

1 Claim, No Drawings

RENIN INHIBITORS, PROCESSES FOR PREPARING THEM, METHODS FOR USING THEM, AND COMPOSITIONS CONTAINING THEM

CROSS-REFERENCE TO RELATED APPLICATION

This application is a divisional of U.S. application Ser. No. 07/384,236 filed Jul. 24, 1989, now U.S. Pat. No. 5,063,207 which is a continuation-in-part of U.S. application Ser. No. 206,023 filed Jun. 17, 1988 now abandoned which is a continuation-in-part of U.S. application Ser. No. 113,772 filed Oct. 26, 1987 now abandoned.

BACKGROUND OF THE INVENTION

Renin is a natural enzyme which is released into the blood from the kidney. It cleaves its natural substrate, angiotensinogen, releasing decapeptide, angiotensin I. This is in turn cleaved by converting enzyme in the lung, kidney and other tissues to an octapeptide, angiotensin II. Angiotensin II raises blood pressure both directly by causing arteriolar constriction and indirectly by stimulating release of the sodium-retaining hormone aldosterone from the adrenal gland causing a rise in extracellular fluid volume. Inhibitors of renins have been sought as an agent for control of hypertension, congestive heart failure, and hyperaldosteronism.

The present invention concerns novel peptides which inhibit renin. It also concerns pharmaceutical compositions containing these novel peptides, methods of treating renin-associated hypertension, congestive heart failure, and hyperaldosteronism, as well as the use of the peptides as diagnostic tools, and the methods for preparing the peptides.

U.S. Pat. No. 4,479,941 covers certain renin-inhibitory peptides of the formula

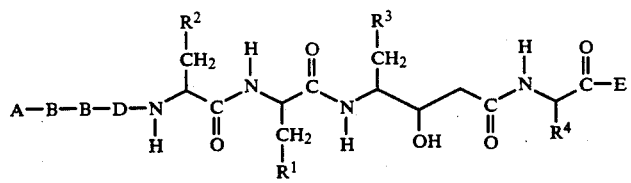

European Application No. 85/308759 covers certain renin-inhibitory dipeptides of the formula

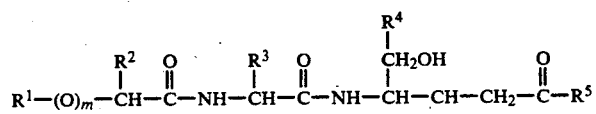

wherein m is 0 or 1 and $R^1$–$R^5$ are a variety of organic groups.

European Application No. 184,855 covers renininhibitory peptides of the formula

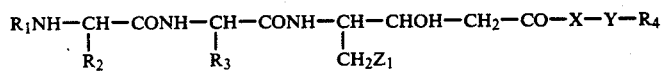

wherein A is an N-protecting group; $R_1$, $R_3$, $R_5$ and $R_7$ are lower alkyl or lipophilic or aromatic amino acid side chains and may be the same or different; $R_2$, $R_4$ and $R_6$ are hydrogen or lower alkyl and may be the same or different; X is hydrogen, lower alkyl or —$CH_2$—$OR_8$, wherein $R_8$ is hydrogen, lower alkyl or alkaryl; and $R_9$ is lower alkyl, hydroxy, hydroxyalkyl, alkoxy, allyl, alkaryloxy or thioalkyl and pharmaceutically acceptable salts thereof.

European Application No. 192,544 covers peptide pepstatin analogues of the formula

wherein $R_1$ is COR or $SO_2R^1$; $R_2$ is optionally substituted lower alkyl, phenyl, naphthyl, cyclohexyl or pyridyl; $R_3$ is hydrogen, lower alkenyl, phenyl, naphthyl, 3-6C cycloalkyl, monocyclic heterocyclic or substituted lower alkyl; $Z_1$ is i-Pr, phenyl, cyclohexyl; X-Y is a dipeptide.

European Application No. 220,665 covers peptidyl; amino cycloalkyl; hydroxy alkanoic acid derivatives of the formula $$X-Z-NR_2-CHR_3-CHOH-(CHR_4)_n-CO-E$$

wherein
X=H, $R_1OC_mH_{2m}CO$, $R_1C_mH_{2m}OCO$, $R_1C_mH_{2m}CO$, $R_1SO_2$, Q-$C_rH_{2r}CO$, $H(NHCH_2CH_2)_mNHCH_2CO$ or 9-fluorenyl-$C_mH_{2m}OCO$;
Z=1-4 peptide-linked aminoacid gps. selected from Abu, Ada, Ala, Arg, Asn, Bia, Cal, Dab, Gln, Gly, His, N(im)-alkyl-His, Ile, Leu, tert-Leu, Lys, Met, α-Nal, β-Nal, Nbg, Nle, Orn, Phe, Pro, Ser, Thr, Tic, Trp, Tyr and Val; and
E=OH, OA, $NH_2$, NHA or $N(A)_2$.

The compounds are useful as renin and acid protease inhibitors.

Since HIV protease, like renin, is an aspartyl protease, these compounds can also be used to treat diseases caused by retroviruses including HTLV-I and -III.

SUMMARY OF THE INVENTION

The present invention relates to novel peptides of the formula $$A - X - Y - W - U \qquad (I)$$

and the pharmaceutically acceptable acid addition salts thereof wherein A, X, Y, W, and U are as defined herein below.

The invention also includes pharmaceutical compositions comprising an effective amount of the above peptide of formula I in admixture with a pharmaceutically acceptable carrier or excipient and a method for treating renin-associated hypertension in a patient suffering therefrom comprising administering to said patient the above pharmaceutical composition in unit dosage form.

Further the invention includes a pharmaceutical composition comprising an effective amount of a peptide of formula I above in admixture with a pharmaceutically acceptable carrier or excipient, and a method for treating hyperaldosteronism in a patient suffering therefrom comprising administering to said patient the above pharmaceutical composition in unit dosage form.

Further the invention includes a pharmaceutical composition comprising an effective amount of a peptide of formula I in admixture with a pharmaceutically acceptable carrier or excipient, and a method for treating congestive heart failure in a patient suffering therefrom comprising administering to said patient the above pharmaceutical composition in unit dosage form.

The present invention also includes the use of peptides of formula I above as diagnostic tools for the identification of cases of hypertension due to renin excess.

The invention further includes methods for preparing peptides of formula I above and novel intermediates used in their preparation.

DETAILED DESCRIPTION

The following table provides a dictionary of the terms used in the description of the invention.

TABLE 1

| Abbreviated Designation | Amino Acid |
|---|---|
| LEU | L-Leucine |
| HIS | L-Histidine |
| TZA | 2-(S)-Amino-3-(4-thiazolyl)-propanoic acid (4-Thiazolylalanine) |
| STA | 4(S)-Amino-3(S)-hydroxy-6-methylheptanoic acid |
| PHSTA | 4(S)-Amino-3(S)-hydroxy-5-phenylpentanoic acid |
| CYSTA | 4(S)-Amino-3(S)-hydroxy-5-cyclohexanepentanoic acid |
| ILE | L-Isoleucine |
| PHE | L-Phenylalanine |
| PHE(OBn) | L-Phenylalanine benzyl ester |
| HOMOPHE | 2(S)-Amino-5-phenylpentanoic acid (Homophenylalanine) |
| LYS | L-Lysine |
| MET | L-Methionine |
| MET(O) | L-Methionine-sulfoxide |
| MET(O₂) | L-Methionine-sulfone |
| NAPHTHYLALA | 2(S)-Amino-3-(1-naphthyl)-propanoic acid (1-Naphthylalanine) |
| CYCLOHEXYLALA | Cyclohexylalanine (Hexahydro-L-phenylalanine) |
| TYR | L-Tyrosine |
| TYR(OMe) | O-Methyl-L-tyrosine |
| TRP | L-Tryptophane |
| GLN | L-Glutamine |
| (NMe)PHE | N-Methyl-L-phenylalanine |
| ASTA | 3(RS), 4(S)-Diamino-6-methylheptanoic acid |
| ACYS | 3(RS), 4(S)-Diamino-5-cyclohexanepentanoic acid |
| CHSTA | 4(S)-Amino-3(S)-hydroxy-4-cyclohexanebutanoic acid |
| DFKSTA | 4(S)-Amino-3-oxo-2,2-difluoro-6-methylheptanoic acid |
| DFSTA | 4(S)-Amino-3-(S)-hydroxy-2,2-difluoro-6-methylheptanoic acid |
| DFKCYS | 4(S)-Amino-3-oxo-2,2-difluoro-5-cyclohexane pentanoic acid |
| DFCYS | 4(S)-Amino-3-(S)-hydroxy-2,2-difluoro-5-cyclohexane pentanoic acid |
| DFKCHS | 4(S)-Amino-3-oxo-2,2-difluoro-4-cyclohexane butanoic acid |
| DFCHS | 4(S)-Amino-3-(S)-hydroxy-2,2-difluoro-4-cyclohexane butanoic acid |
| ALG | 2(S)-Amino-4-pentenoic acid (Allylglycine) |
| PGY | 2(S)-Aminopentanoic acid (Propylglycine) |
| PPG | 2(S)-Amino-4-pentynoic acid (Propargylglycine) |
| CPM | 2(S)-Amino-3-cyclopropane-propanoic acid (Cyclopropylalanine) |
| EMG | 2(S)-Amino-4,5(RS)-epoxy-4-pentenoic acid |
| BYG | 2(S)-Aminohexanoic acid (Butylglycine) |
| NIA | 2(S)-Amino-3-cyanopropanoic acid (cyanoalanine) |
| PHA | 2(S)-Amino-6-(1-pyrrolo) hexanoic acid |
| | Amides With |
| —NHCH₂Ph | Benzylamine |
| —NHCH₂— 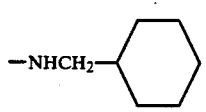 | Cyclohexylmethylamine |

TABLE 1-continued

| Abbreviated Designation | | |
|---|---|---|
| —NHCH$_2$—C$_6$H$_4$—CH$_2$NHZ (BOC) | | m-Xylene-di-amine (Z or BOC) |
| —NHCH$_2$—C$_6$H$_4$—CH$_2$NH$_2$ | | m-Xylene-di-amine |
| —NH$_2$ | | Ammonia |
| —NH—(4-piperidinyl)—N—CH$_2$Ph | | 4-Amino-N-benzylpiperidine |
| —NH—(4-piperidinyl)—NH | | 4-Aminopiperidine |
| —NHCH$_2$CH$_2$-(2-pyridyl) | | 2-Aminoethylpyridine |
| —NHCH$_2$CH$_2$—N(morpholino) | | 2-Aminomethylpyridine |
| —NH—CH$_2$-(2-pyridyl) | | N-(2-Aminoethyl)morpholine |
| —NHCH$_2$CHCH$_2$CH$_3$ \| CH$_3$ | | 2-Methylbutylamine |
| —NHCH—CH(CH$_3$)CH$_2$CH$_3$ \| CH$_2$OH | | 1-Hydroxymethyl-2-methylbutylamine |
| —NHCH$_2$CH$_2$N(CH$_2$CH$_2$OH)$_2$ | | 2-(Bis(2-Hydroxyethyl)amino)-ethylamine |
| —N(morpholino) | | Morpholine |

| | Protecting Group |
|---|---|
| Z | Benzyloxycarbonyl |
| BOC | Tert-butyloxycarbonyl |
| TR | Triphenylmethyl |
| TBS | t-Butyldimethylsilyl |
| | Esters With |
| —OCH$_3$ | Methanol |
| —OC$_2$H$_5$ | Ethanol |
| —OCH(CH$_3$)$_2$ | 2-Propanol |
| —OC(CH$_3$)$_3$ | tert-Butanol |
| | Solvents and Reagents |
| DMF | N,N-Dimethylformamide |
| DMSO | Dimethylsulfoxide |
| HOBT | Hydroxybenzotriazole |
| DCC | N,N'-Dicyclohexylcarbodiimide |
| HOAc | Acetic acid |
| Et$_3$N | Triethylamine |
| THF | Tetrahydrofuran |

TABLE 1-continued

| Abbreviated Designation | |
|---|---|
| CH$_2$Cl$_2$ | Dichloromethane |

The peptides of the present invention are represented by the formula $$A\text{-}X\text{-}Y\text{-}W\text{-}U \qquad I$$

and the pharmaceutically acceptable acid addition salts thereof, wherein A is

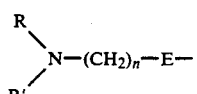

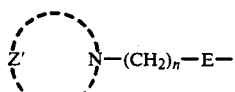

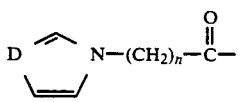

wherein R and R' are each independently hydrogen or lower alkyl;

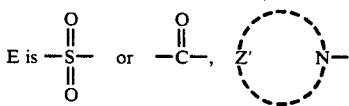

is a saturated ring of from 1 to 5 carbon atoms wherein Z' is CH$_2$, O, S, or NR,
n is an integer of from 0 to 3; and
D is N, S, O, or CH.
Examples of A may be but are not limited to the following:

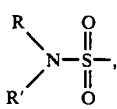

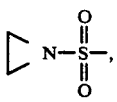

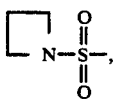

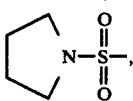

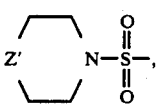

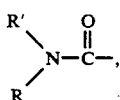

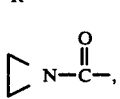

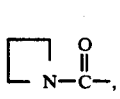

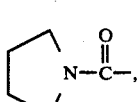

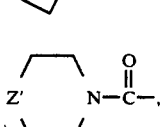

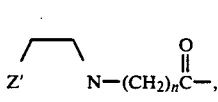

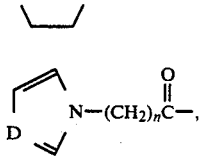

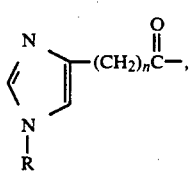

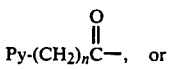

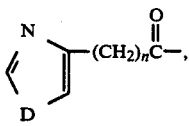

wherein
R and R' are each independently hydrogen or lower alkyl;
Z' is CH$_2$, O, S, NH, NR with R defined as above;
n is 0-3;
D is N, S, O, CH;
Py is 2-pyridyl, 3-pyridyl, or 4-pyridyl.
X is PHE, HOMOPHE, TYR, TYR(OMe), NAPHTHYLALA, CYCLOHEXYLALA, LEU, TRP, HIS, or (NMe)PHE;
Y is GLN, HIS, LEU, PGY, MET MET(O), MET(O$_2$), TZA, ALG, PPG, CPM, EMG, BYG, NIA, PHA, .

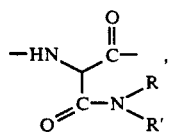

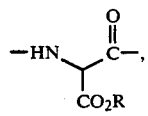

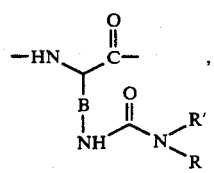

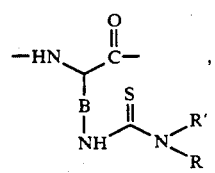

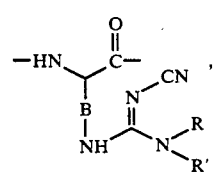

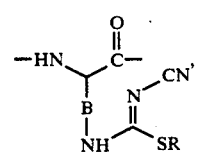

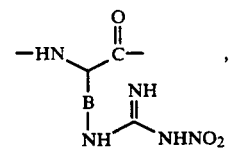

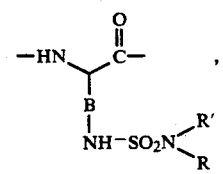

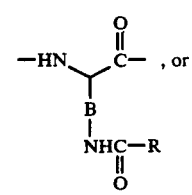

-continued

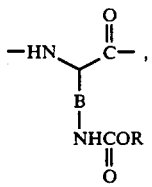

wherein
R and R' are each independently H, benzyl, or lower alkyl;
B is a chain of from three to six carbon atoms which is saturated, olefinic, or acetylenic;
W is STA, CYSTA, or PHSTA, CHSTA, DFSTA, DFKSTA, DFCYS, DFKCYS, DFCHS, DFKCHS, ASTA, or ACYS;

U is

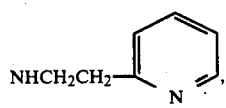

NHCH₂CH₂N(CH₂CH₂OH)₂,

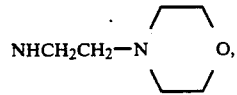

NHCH₂CH(CH₃)CH₂CH₃,

NHCHCH₂(OH)CH(CH₃)CH₂CH₃,

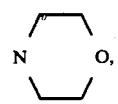

LEU—NHCH₂Ph,

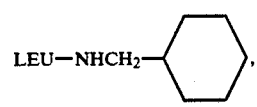

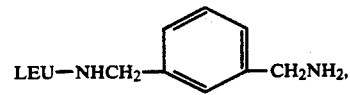

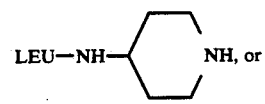

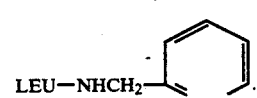

Preferred compounds of the present invention are those wherein A is Me₂N-E-,

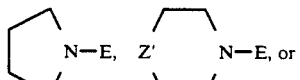 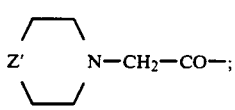

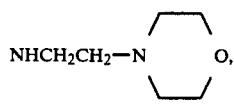

X is PHE, TYR(OMe) or NAPHTHYLALA, W is STA, CHSTA, DFKCYS, DFCYS, DFSTA, DFKSTA or CYSTA, U is

NHCH$_2$CH$_2$N(CH$_2$CH$_2$OH)$_2$ or
NHCH$_2$CH(CH$_3$)CH$_2$CH$_3$, and Y is HIS,

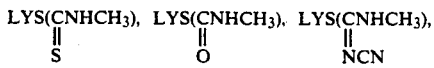

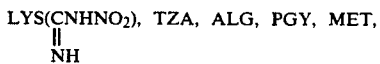

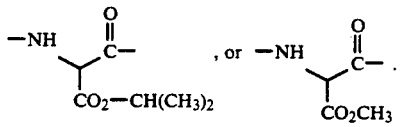

Particularly valuable compounds falling within the scope of the invention include the following:

Me$_2$NSO$_2$—TYR(OMe)—HIS—STA—NHCH$_2$CH(CH$_3$)CH$_2$CH$_3$,

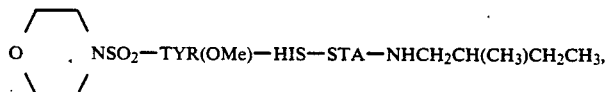

Me$_2$NCO—PHE—HIS—STA—NHCH$_2$CH(CH$_3$)CH$_2$CH$_3$,

Me$_2$NCO—TYR(OMe)—HIS—STA—NHCH$_2$CH(CH$_3$)CH$_2$CH$_3$,

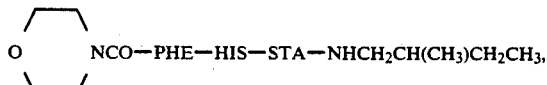

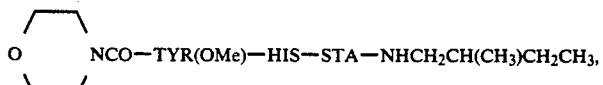

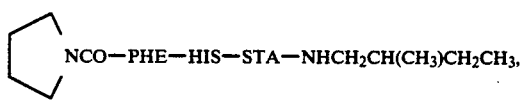

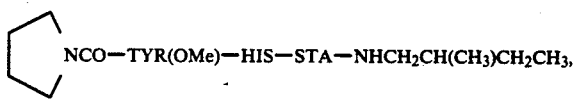

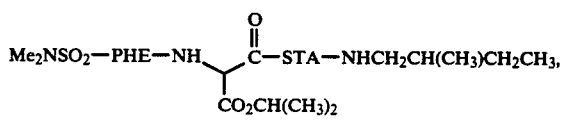

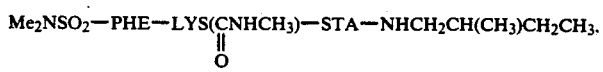

-continued
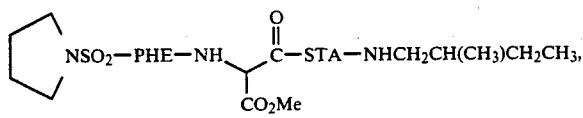
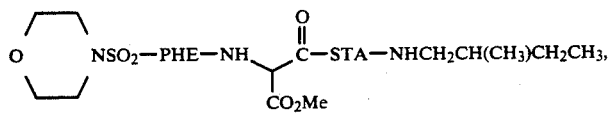
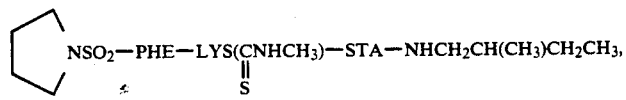
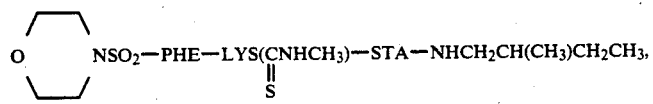
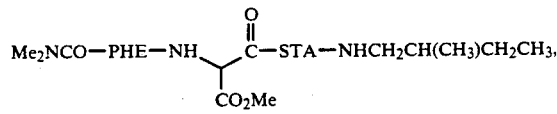
Me₂NCO—PHE—LYS(CNHCH₃)—STA—NHCH₂CH(CH₃)CH₂CH₃,
            ‖
            S
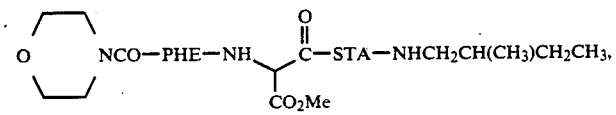
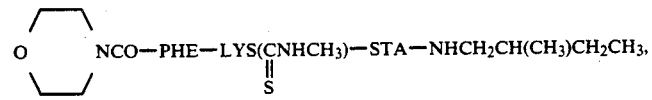
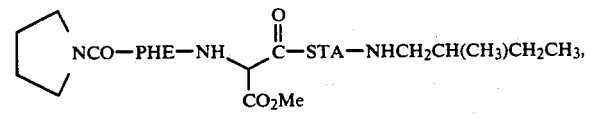
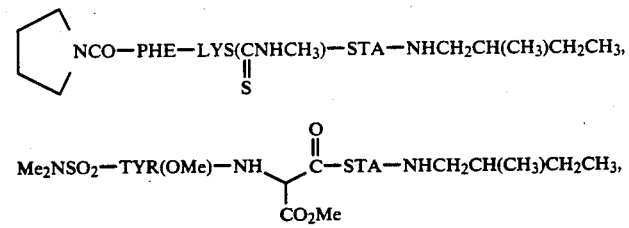
Me₂NSO₂—TYR(OMe)—LYS(CNHCH₃)—STA—NHCH₂CH(CH₃)CH₂CH₃,
                     ‖
                     S
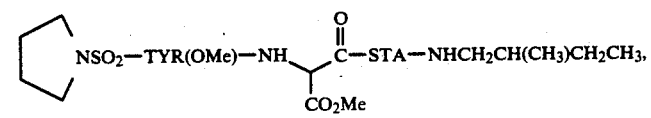
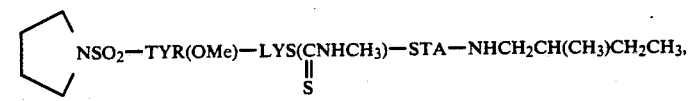

-continued
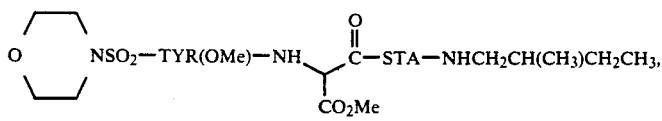
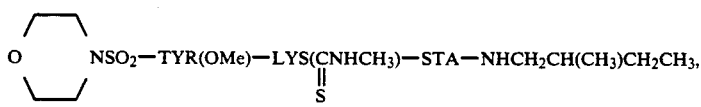
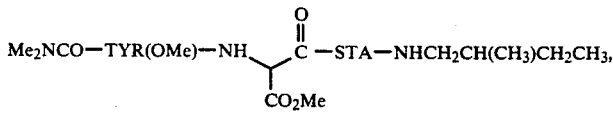
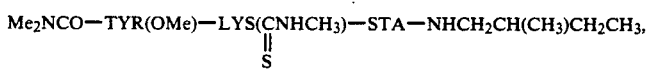
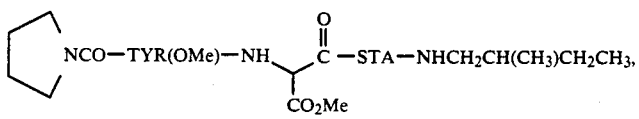
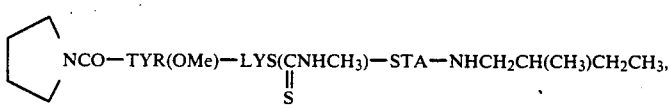
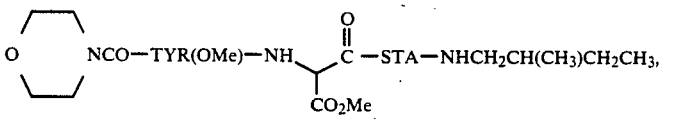
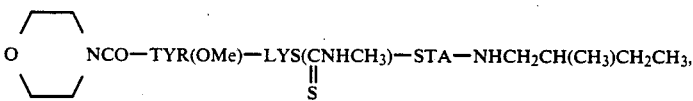
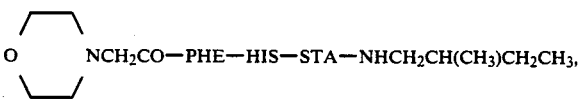
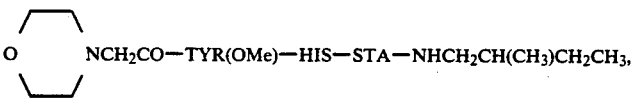
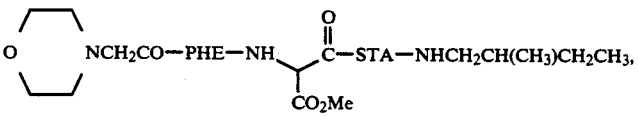
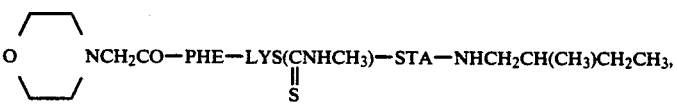
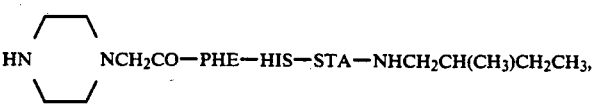

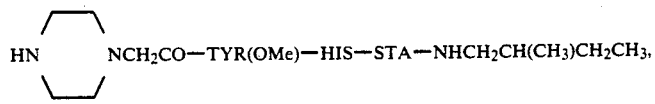
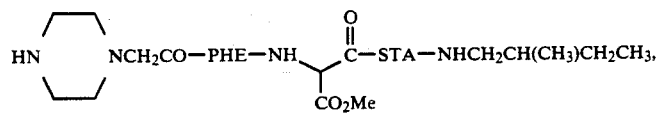
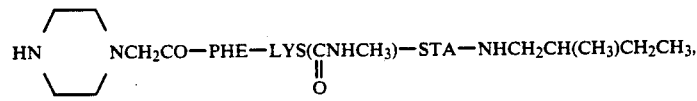
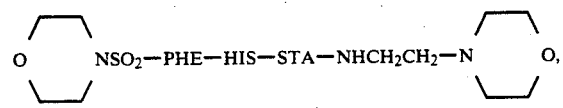
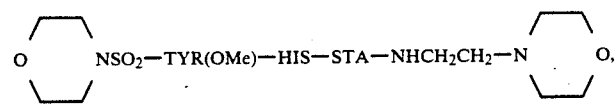
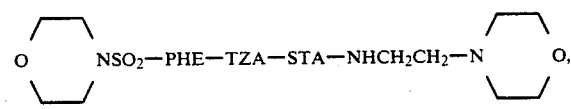
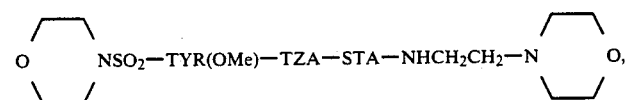
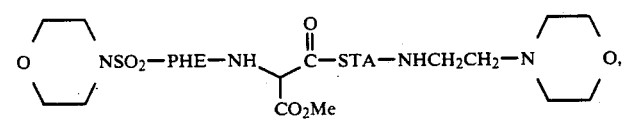
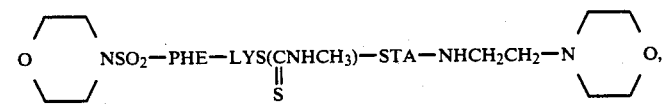
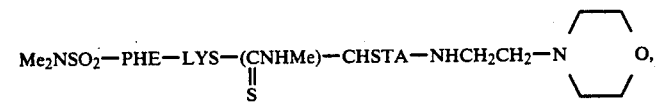
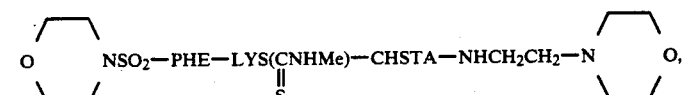
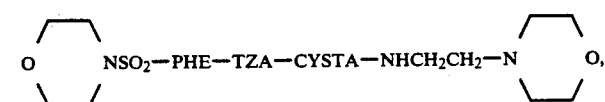
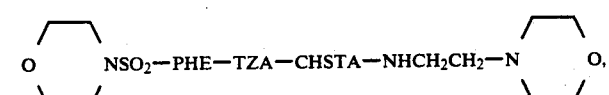

-continued
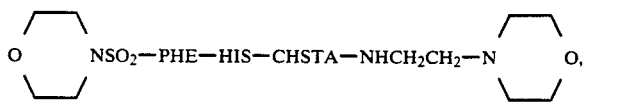
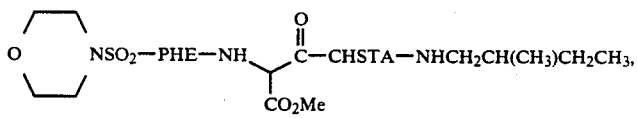
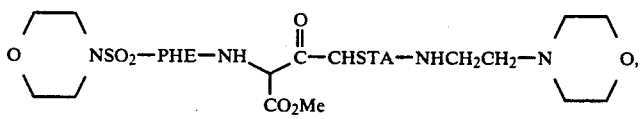
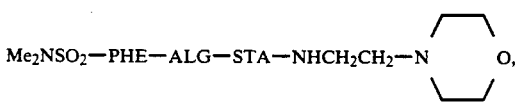
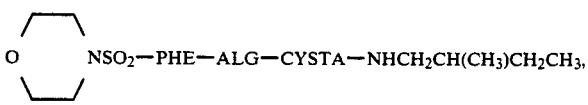
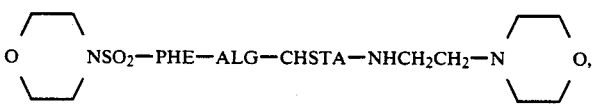
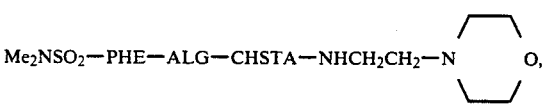
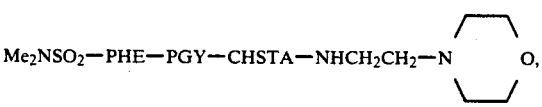
Me₂NSO₂—PHE—PGY—CHSTA—NHCH₂CH(CH₃)CH₂CH₃,
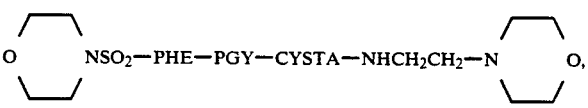
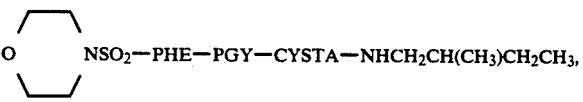
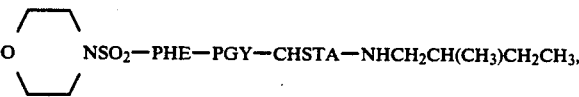
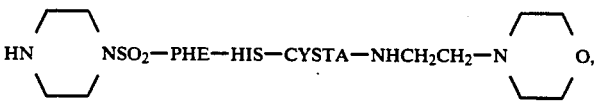

-continued
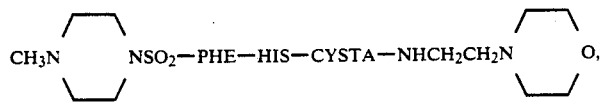
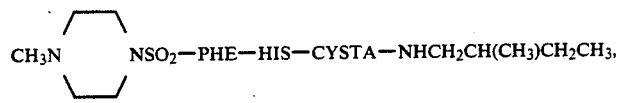
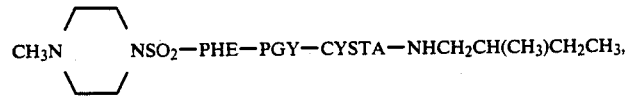
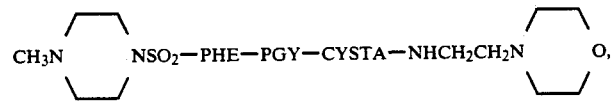
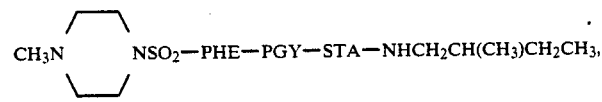
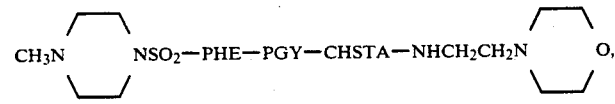
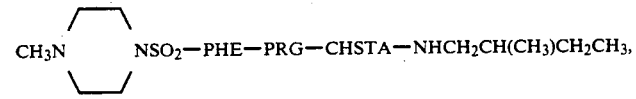
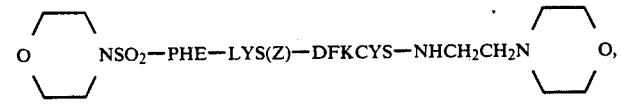
Me$_2$NSO$_2$—PHE—NIA—STA—NHCH$_2$CH(CH$_3$)CH$_2$CH$_3$,
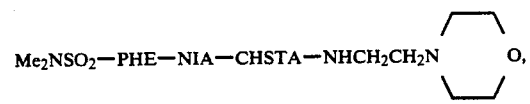
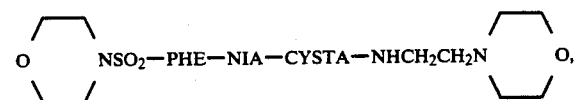
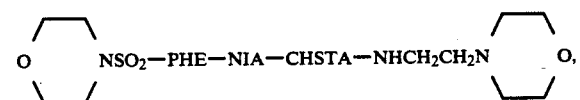
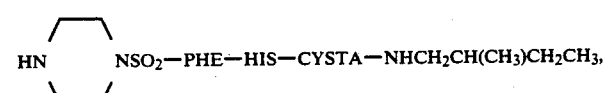
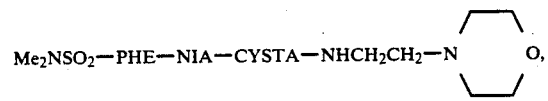

-continued
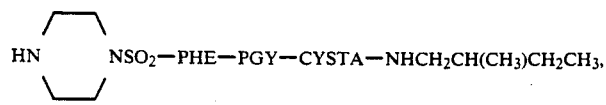
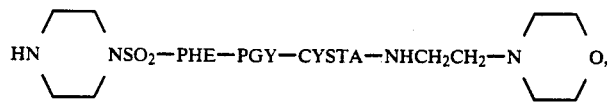
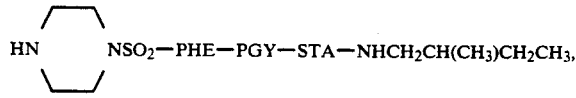
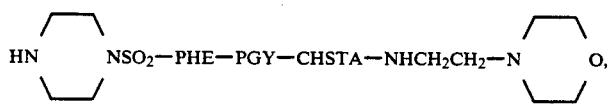
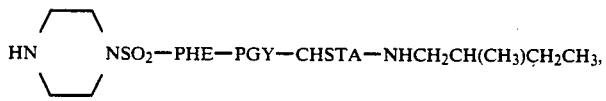
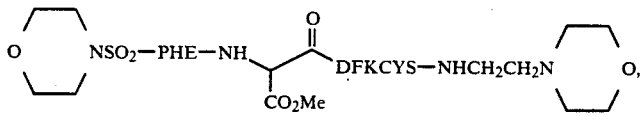
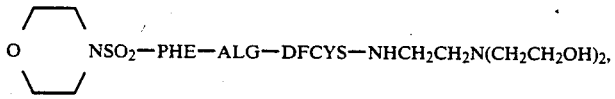
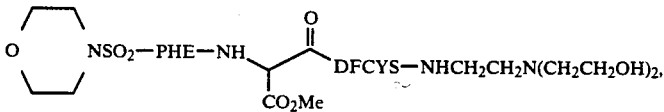
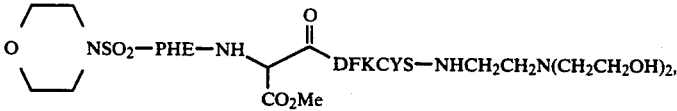
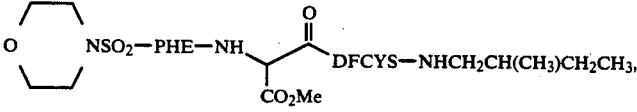
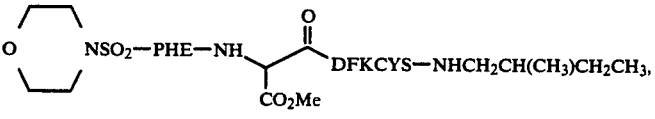
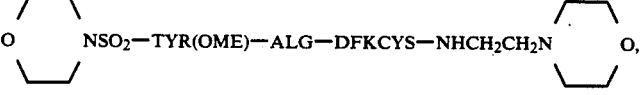

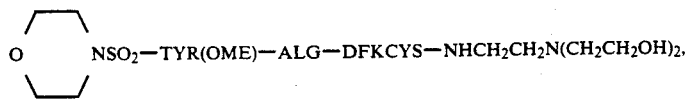
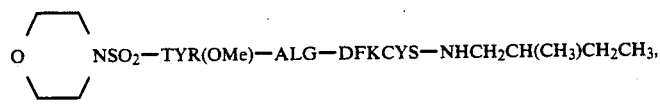
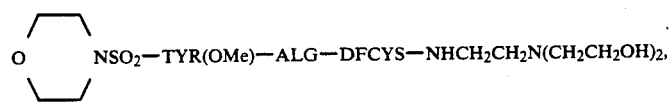
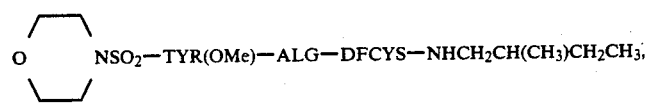
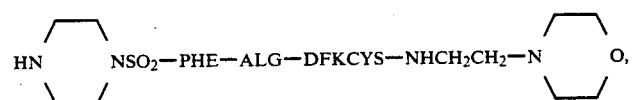
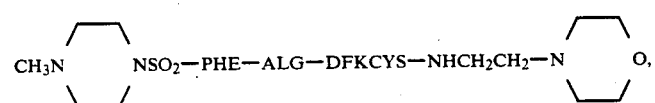
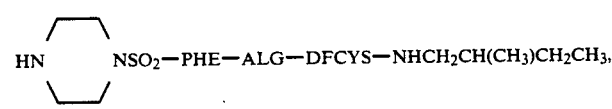
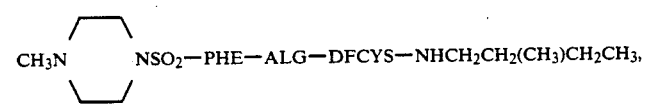
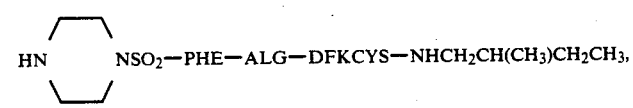
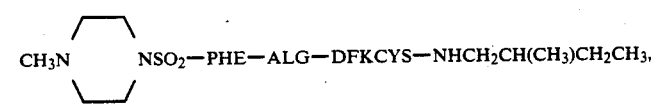
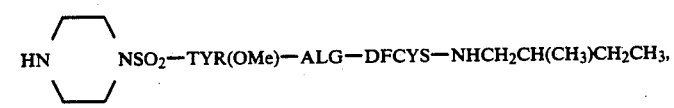
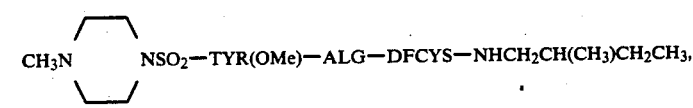
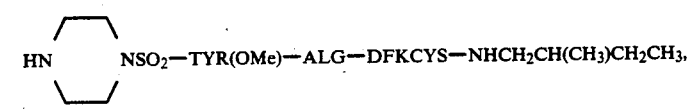
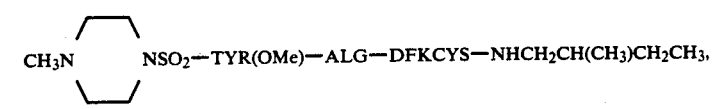

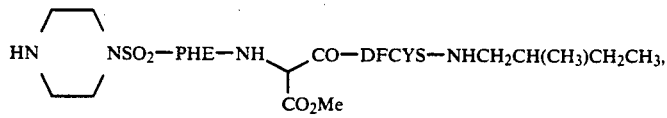
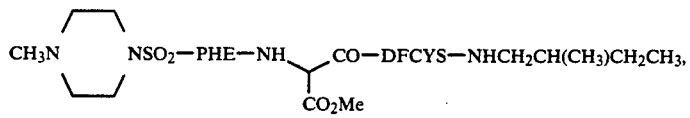
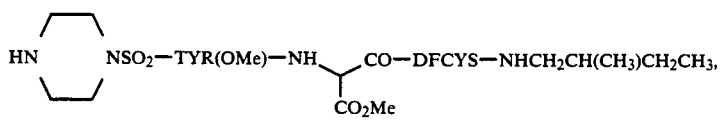
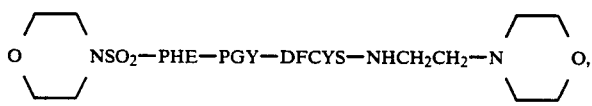
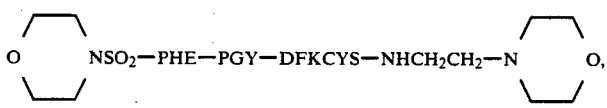
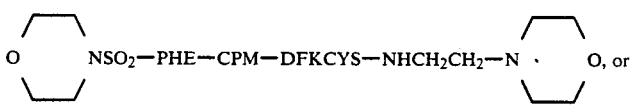
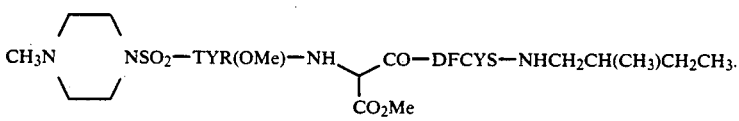
Most preferred compounds of the invention are:
Me₂NSO₂—PHE—HIS—STA—NHCH₂CH(CH₃)CH₂CH₃,
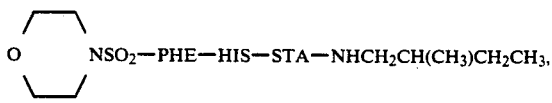
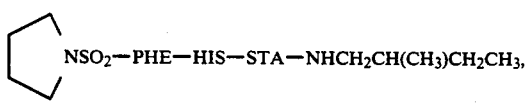
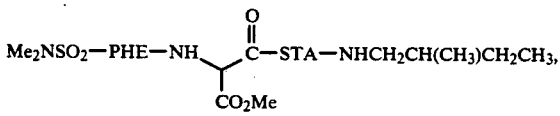
Me₂NSO₂—PHE—LYS(CNHCH₃)—STA—NHCH₂CH(CH₃)CH₂CH₃,
               ‖
               S
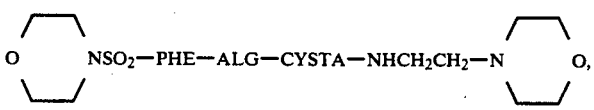

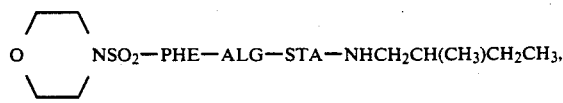NSO₂—PHE—ALG—STA—NHCH₂CH(CH₃)CH₂CH₃,

Me₂NSO₂—PHE—ALG—CYSTA—NHCH₂CH₂—N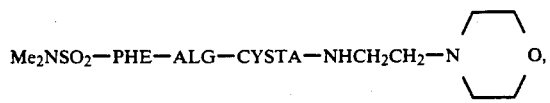O,

Me₂NSO₂—PHE—ALG—STA—NHCH₂CH(CH₃)CH₂CH₃,

Me₂NSO₂—PHE—ALG—CYSTA—NHCH₂CH(CH₃)CH₂CH₃,

Me₂NSO₂—PHE—PGY—STA—NHCH₂CH(CH₃)CH₂CH₃,

Me₂NSO₂—PHE—PGY—CYSTA—NHCH₂CH(CH₃)CH₂CH₃,

Me₂NSO₂—PHE—PGY—CYSTA—NHCH₂CH₂—N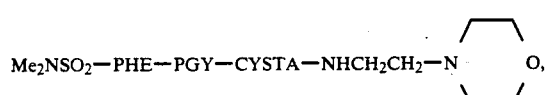O,

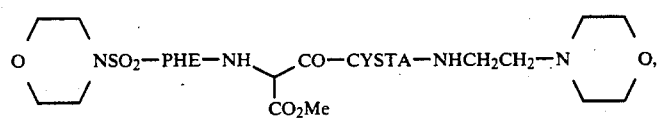NSO₂—PHE—NH—CH(CO₂Me)—CO—CYSTA—NHCH₂CH₂—N O,

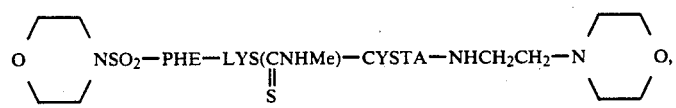NSO₂—PHE—LYS(CNHMe)—CYSTA—NHCH₂CH₂—N O,
                        ‖
                        S Me₂NSO₂—PHE—LYS(CNHMe)—CYSTA—NHCH₂CH₂—N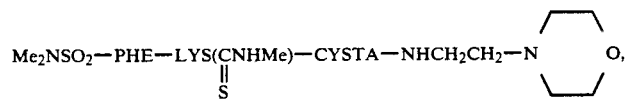O,
                  ‖
                  S Me₂NSO₂—PHE—HIS—CYSTA—NHCH₂CH₂—N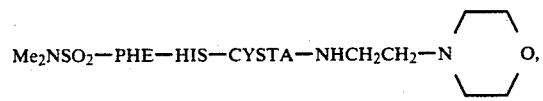O, Me₂NSO₂—PHE—MET—CHSTA—NHCH₂CH(CH₃)CH₂CH₃,

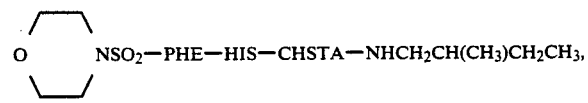NSO₂—PHE—HIS—CHSTA—NHCH₂CH(CH₃)CH₂CH₃,

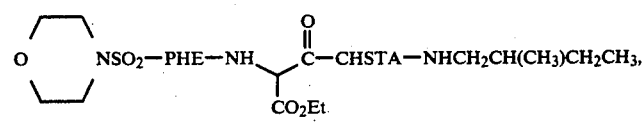NSO₂—PHE—NH—CH(CO₂Et)—C(O)—CHSTA—NHCH₂CH(CH₃)CH₂CH₃,

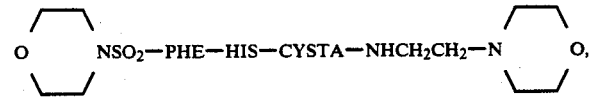NSO₂—PHE—HIS—CYSTA—NHCH₂CH₂—N O,

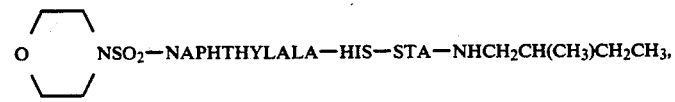NSO₂—NAPHTHYLALA—HIS—STA—NHCH₂CH(CH₃)CH₂CH₃,

HN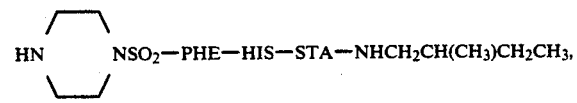NSO₂—PHE—HIS—STA—NHCH₂CH(CH₃)CH₂CH₃,

-continued
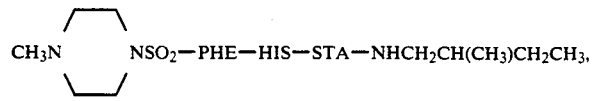
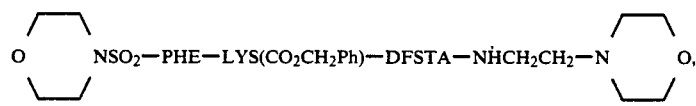
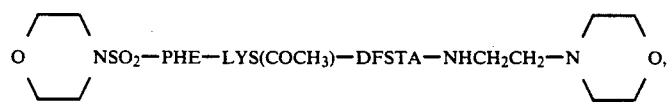
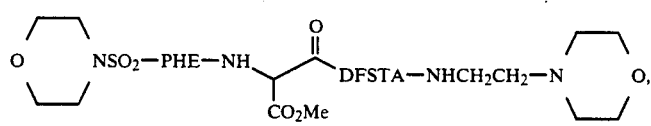
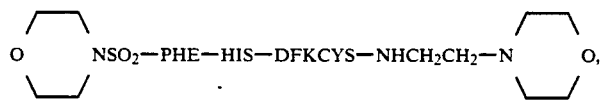
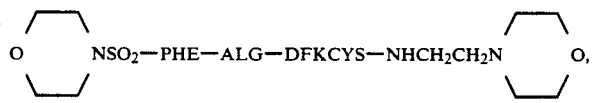
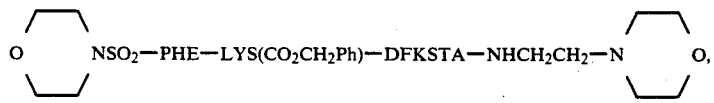
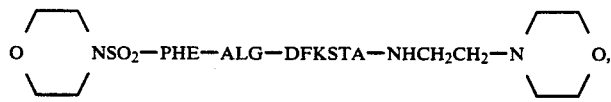
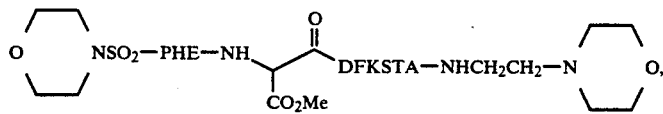
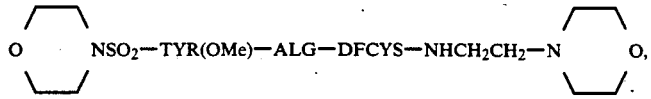

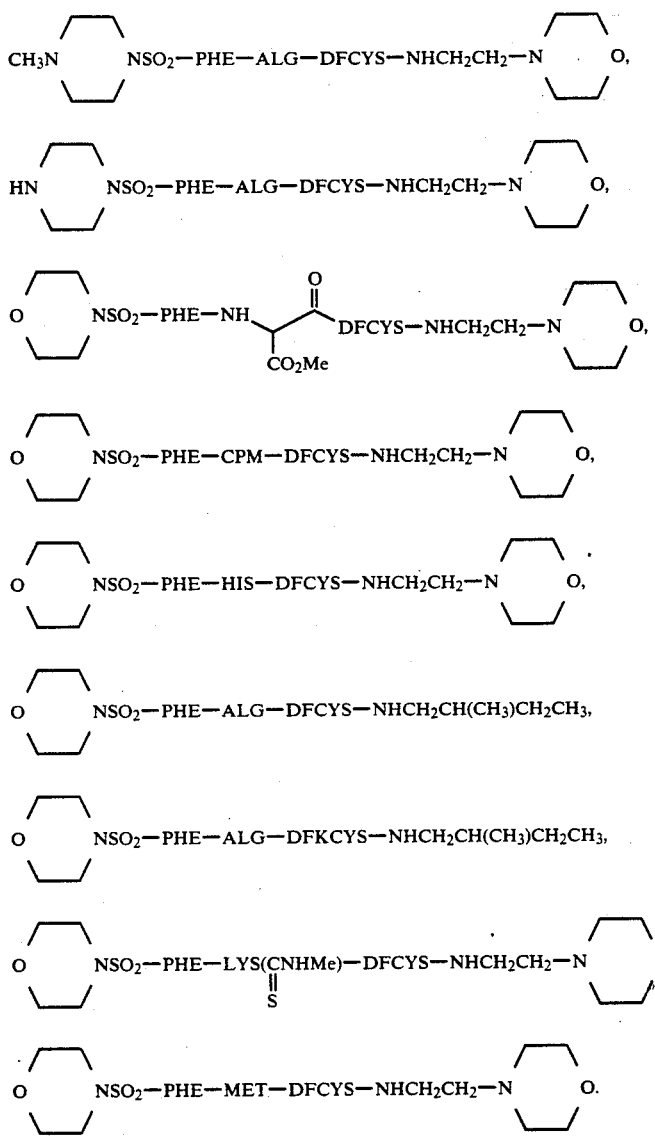

The compounds of the present invention have the advantage of increased hydrophilicity relative to renin inhibitors known in the art. This property makes the compounds more readily absorbed.

The compounds include solvates and hydrates and pharmaceutically acceptable acid addition salts of the basic compounds of formula I above.

The term pharmaceutically acceptable acid addition salt is intended to mean a relatively nontoxic acid addition salt either from inorganic or organic acids such as, for example, hydrochloric, hydrobromic, hydroiodic, sulfuric, phosphoric, acetic, citric, oxalic, malonic, salicylic, malic, benzoic, gluconic, fumaric, succinic, ascorbic, maleic, tartaric, methanesulfonic, and the like. The salts are prepared by contacting the free base form with a sufficient amount of the desired acid to produce a salt in the conventional manner. The free base forms may be regenerated by treating the salt form with a base. Unless otherwise specified the L form is the preferred embodiment.

The modified peptides of the present invention possess one or more chiral centers and each center may exist in the R(D) or S(L) configuration. The present invention includes all enantiomeric and epimeric forms as well as the appropriate mixtures thereof.

Some of the above novel peptides may be prepared in accordance with well-known procedures for preparing peptides from their constituent amino acids. Other of the novel peptides of the present invention are prepared by a step-wise procedure or by a fragment coupling procedure depending upon the particular final product desired.

The following scheme illustrates novel methods of preparing certain peptides of the present invention.

Scheme 1

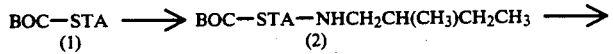

-continued
Scheme I

STA—NHCH$_2$CH(CH$_3$)CH$_2$CH$_3$ ⟶ BOC—LYS(Z)—STA—NHCH$_2$CH(CH$_3$)CH$_2$CH$_3$ ⟶
(3) (4)

LYS(Z)—STA—NHCH$_2$CH(CH$_3$)CH$_2$CH$_3$ ⟶ Me$_2$NSO$_2$—PHE—LYS(Z)—STA—NHCH$_2$CH(CH$_3$)CH$_2$CH$_3$ ⟶
(5) (6)

Me$_2$NSO$_2$—PHE—LYS—STA—NHCH$_2$CH(CH$_3$)CH$_2$CH$_3$ ⟶
(7)

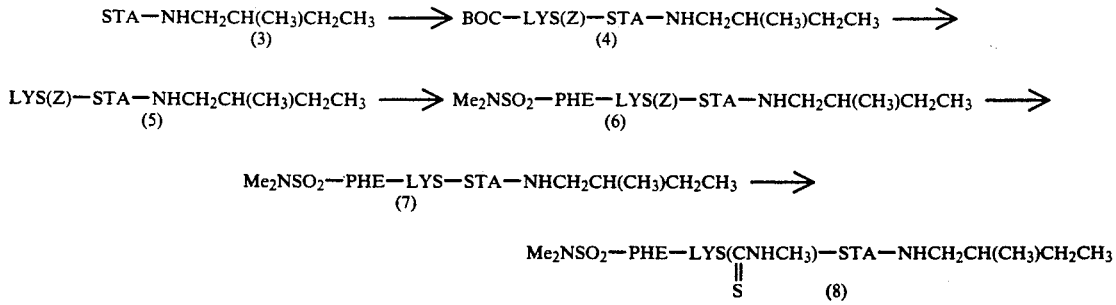

According to Scheme I above, BOC-protected statine (1) is reacted with DCC, HOBT, and a primary amine, for example, 2-methylbutylamine, to form the corresponding BOC-protected compound (2). The reaction takes place in an inert solvent such as methylene chloride, tetrahydrofuran, chloroform, dioxane, or ethyl acetate. The preferred solvent is methylene chloride. The reaction time varies from 1 to 24 hours. Preferably it takes about 2 to 6 hours. The reaction temperature may also vary from about 15° C. to 30° C. Preferably it is approximately 25° C.

The above compound (2) is reacted with a strong acid such as trifluoroacetic, HBr, or HCl to remove the BOC-protecting group thus forming corresponding compound (3) with a free amino terminus. Preferably HCl is used.

Compound 3 is then reacted with BOC-protected LYS(Z) to form the corresponding compound (4). This reaction takes place in an inert solvent, for example DMF, with DCC, HOBT, and triethylamine as activating agents at temperatures of from 0° C. to 25° C. The reaction may take as long as 72 hours.

This compound (4) is reacted with a strong acid, such as trifluoroacetic acid, to form the corresponding compound with a free amino terminus (5). The reaction takes place in an inert solvent, preferably dichloromethane, at about 25° C, taking from 0.5 to 2 hours.

This compound (5) is reacted with L-N,N-dimethylsulfamylphenylalanine, DCC, and HOBT in an inert solvent such as DMF at approximately room temperature for from 4 to 24 hours to form the Z-protected tripeptide (6). The Z group is then removed by catalytic hydrogenation in a polar, inert solvent such as methanol forming peptide (7). The catalyst is preferably palladium on carbon.

This peptide (7) is reacted with an acylating agent such as methyl isocyanate, methyl isothiocyanate, acetyl chloride, methyl chloroformate, N,N-dimethylsulfamyl chloride, or 2-methyl-1-nitro-2-thiopseudourea at about room temperature in an inert solvent such as methylene chloride to form a compound of the present invention (8).

For compounds of the types illustrated in Examples 3-15 other amino acid derivatives such as a protected HIS derivative (e.g. N$_{(\tau)}$-trityl, N$_{(\alpha)}$-Z), a BOC-protected allylglycine or a BOC-protected aminomalonate monomethyl ester are substituted for the protected LYS derivative in the conversion of statine derivative (3) to dipeptide (4). Additionally, carbamyl or acyl amino acid derivatives may be substituted for sulfamyl amino acid derivatives in the conversion of dipeptide (5) to tripeptide (6). Finally, amides of CYSTA, CHSTA, DFSTA, DFCYS or DFCHS may replace STA amides.

Sulfamyl amino acid derivatives are prepared by reaction of a sulfamyl chloride with the desired amino acid in a mixture of aqueous base and organic solvents at 0° to 40° C. Bases include NaOH, NaHCO$_3$, Na$_2$CO$_3$, KOH, KHCO$_3$, K$_2$CO$_3$. Organic solvents include THF, dioxane, and acetonitrile.

Alternatively, sulfamyl amino acids are prepared by reaction of a sulfamyl chloride with the tetra-alkylammonium salt of the desired aminoacid in anhydrous organic solvents at 0° to 40° C. Salts include tetra-n-butylammonium, tetra-n-propylammonium, tetraethylammonium, tetramethylammonium and benzyltrimethylammonium. Organic solvents include THF, dioxane, 1,2-dimethoxyethane, acetonitrile, 2-propanol, t-butanol, chloroform, dichloromethane and 1,2-dichloroethane.

Carbamyl amino acid derivatives are prepared by reaction of a carbamyl chloride, organic base, and an amino acid ester in an aprotic solvent, followed by saponification or hydrogenolysis of the ester. Bases include triethyl amine, diisopropyl ethyl amine, pyridine, and 4-dimethylaminopyrido. Solvents include dichloromethane, THF, chloroform, acetonitrile, and dioxane.

An alternative method of synthesis is shown in Scheme II wherein BOC-LYS(Z)-STA-NHCH$_2$CH(CH$_3$)CH$_2$CH$_3$ (4), prepared as in Scheme I, is treated with hydrogen and palladium on carbon catalyst in an inert, polar solvent such as methanol to give the compound with a free amino side chain (9).

Acylation of this compound (9) with acylating agents such as in the final step of the previous method affords LYS-derivatized peptides such as the thiourea (10).

This compound (10) is treated with strong acid such as methanolic hydrogen chloride in an inert solvent, preferably dichloromethane, at about 25° C., taking 10 to 60 minutes to remove the BOC-protecting group.

The resulting compound (11) is reacted with an amino acid derivative such as L-N,N-dimethylsulfamylphenylalanine, DCC, and HOBT in a polar solvent such as DMF, at about 25° C., for 24 to 48 hours to form a compound of the present invention (8).

Scheme II

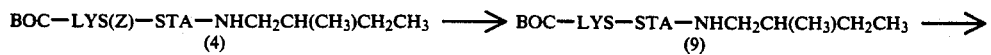

-continued
Scheme II

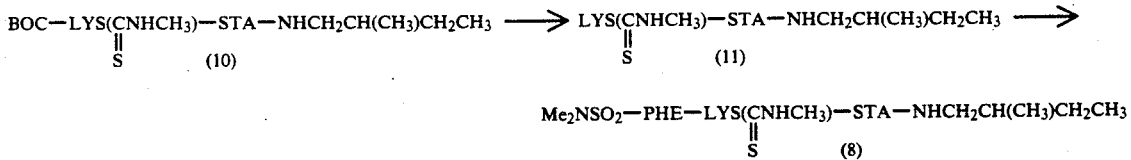

The strategy of peptides chain assembly and selection and removal of protecting groups is discussed in Chapter 1, "The Peptide Bond," in "The Peptides. Analysis, Synthesis, Biology," E. Gross and J. Meienhofer, Eds., Academic Press, New York, NY, 1979, pp. 42-44.

The DCC/HOBT method of coupling is well-known to those skilled in the art and is discussed in Chapter 5, "The Carbodiimide Method" by D. H. Rich and J. Singh in "The Peptides. Analysis, Synthesis, Biology," E. Gross and J. Meienhofer, Eds., Academic Press, New York, NY, 1979, pp. 42-44.

Peptide coupling depends on activating the carboxy terminus and condensing it with another peptide containing a free amino terminus. In addition to the DCC coupling method described above, other methods of activating the carboxyl group of a protected amino acid include:
1) The azide method—described in Chapter 4 of the above reference.
2) The mixed anhydride method—described in Chapter 6 of the above reference.
3) The active ester method—described in Chapter 3 of the above reference.

The invention includes a process for the preparation of compounds of formula I wherein A is

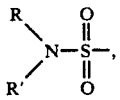

which comprises reacting at least two equivalents of a sulfamyl chloride with at least one equivalent of amino acid as in X, an inorganic aqueous base and a water-miscible organic solvent to give a sulfamyl-amino acid, followed by coupling of the latter to the -Y-W-U fragment and converting if desired to a pharmaceutically acceptable acid addition salt thereof by known means.

The invention also includes a second process for the preparation of compounds of formula I where A is

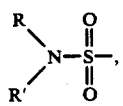

which comprises reacting at least two equivalents of a tetra-alkylammonium salt of an amino acid with one equivalent of a sulfamyl chloride in anhydrous organic solvents to give a sulfamyl amino acid, followed by coupling of the latter to the -Y-W-U fragment and converting, if desired, to a pharmaceutically acceptable addition salt thereof by known means.

The invention also includes a process for the preparation of compounds of formula I wherein A is

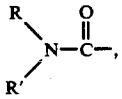

which comprises reacting at least one equivalent of a carbamyl chloride with at least one equivalent of an amino acid benzyl ester as in X, an organic base and an aprotic organic solvent to produce a carbamyl amino acid benzyl ester, hydrogenolysis in the presence of a noble metal catalyst to give a carbamyl amino acid, and subsequent coupling of the latter to the -Y-W-U fragment and converting if desired to a pharmaceutically acceptable acid addition salt thereof by known means.

The invention also includes novel sulfamyl-amino acid intermediates including specifically:

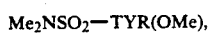

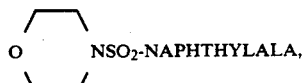

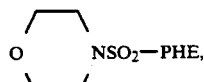

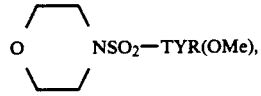

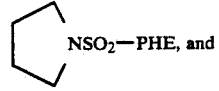

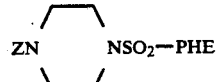

as both the free acid and as salts prepared from alkaline earth metals, ammonia and organic amines, especially dicyclohexylamine.

The compounds of the present invention are useful for treating renin-associated hypertension, congestive heart failure, and hyperaldosteronism. They are also useful as diagnostic tools for determining the presence of renin-associated hypertension or hyperaldosteronism.

The term lower alkyl refers to straight or branched chain alkyl radicals containing from 1 to 6 carbon atoms including but not limited to methyl, ethyl, n-propyl, isopropyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl, and the like.

Pharmaceutical compositions which comprise an effective amount of the compound in combination with a pharmaceutically acceptable carrier are part of the present invention. An important aspect of the present invention is a method of treating renin-associated hypertension in a mammal which comprises administering a pharmaceutical composition containing an effective amount of a compound of the invention in combination with a pharmaceutically acceptable carrier to the mammal.

Another equally important aspect of the present invention is a method of treating hyperaldosteronism in a mammal which comprises administering a pharmaceutical composition containing an effective amount of a compound of the invention in combination with a pharmaceutically acceptable carrier to the mammal.

An additional aspect of the present invention is a method for treating congestive heart failure in a mammal which comprises administering a pharmaceutical composition containing an effective amount of a compound in combination with a pharmaceutically acceptable carrier to the mammal.

The effectiveness of the aforementioned compounds is determined by a test for in vitro renin inhibitory activity. This activity is determined by a standard radioimmunoassay for angiotensin I. In this assay the enzyme, renin, incubated for two hours at 37° in the presence of a substrate, angiotensinogen, generates the product, angiotensin I. Test compounds are added to the incubation mixture. Relative activity is reported as the $IC_{50}$, which is the molar concentration of test compound causing a 50% inhibition of the renin activity.

TABLE 2

| Compound | $IC_{50}$ (M) |
|---|---|
| $Me_2NSO_2$—PHE—HIS—STA—$NHCH_2CH(CH_3)CH_2CH_3$ | $4.1 \times 10^{-8}$ |
|  $O\phantom{XX}NSO_2$—PHE—HIS—STA—$NHCH_2CH(CH_3)CH_2CH_3$ | $2.0 \times 10^{-8}$ |
| $Me_2NSO_2$—TYR(OMe)—HIS—STA—$NHCH_2CH(CH_3)CH_2CH_3$ | $\approx 3.0 \times 10^{-6}$ |
|  $NSO_2$—PHE—HIS—STA—$NHCH_2CH(CH_3)CH_2CH_3$ | $5.8 \times 10^{-8}$ |
| $Me_2NSO_2$—PHE—NH—C(=O)(CO_2Me)—STA—$NHCH_2CH(CH_3)CH_2CH_3$ | $2.5 \times 10^{-8}$ |
| $Me_2NSO_2$—PHE—LYS(CNHCH_3)(=S)—STA—$NHCH_2CH(CH_3)CH_2CH_3$ | $2.5 \times 10^{-8}$ |
| 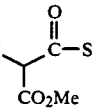 $O\phantom{XX}NCO$—PHE—HIS—STA—$NHCH_2CH(CH_3)CH_2CH_3$ | $3.3 \times 10^{-7}$ |
|  $NCO$—PHE—HIS—STA—$NHCH_2CH(CH_3)CH_2CH_3$ | $4.9 \times 10^{-7}$ |
|  $O\phantom{XX}NCH_2CO$—PHE—HIS—STA—$NHCH_2CH(CH_3)CH_2CH_3$ | $2.5 \times 10^{-7}$ |
| $MeNSO_2$—PHE—ALG—STA—$NHCH_2CH(CH_3)CH_2CH_3$ | $7.0 \times 10^{-9}$ |
| $Me_2NSO_2$—PHE—ALG—CYSTA—$NHCH_2CH(CH_3)CH_2CH_3$ | $1.5 \times 10^{-9}$ |
| $Me_2NSO_2$—PHE—PGY—CYSTA—$NHCH_2CH(CH_3)CH_2CH_3$ | $1.1 \times 10^{-9}$ |
|  $O\phantom{XX}NSO_2$—PHE—NH—CH(CO_2Me)—CO—CYSTA—$NHCH_2CH_2$—N 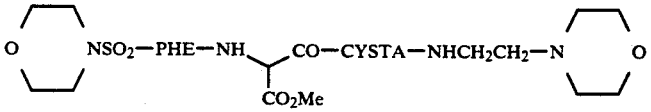 $O$ | $4.0 \times 10^{-9}$ |

TABLE 2-continued

| Compound | IC$_{50}$ (M) |
|---|---|
| Me$_2$NSO$_2$—PHE—LYS(CNHMe)—CYSTA—NHCH$_2$CH$_2$—N(morpholino) (with C=S on LYS substituent) | $2.0 \times 10^{-8}$ |
| (morpholino)O—NSO$_2$—PHE—LYS(CO$_2$CH$_2$Ph)—DFKSTA—NHCH$_2$CH$_2$—N(morpholino) | $2.2 \times 10^{-9}$ |
| Me$_2$NSO$_2$—PHE—HIS—CYSTA—NHCH$_2$CH$_2$—N(morpholino) | $2.0 \times 10^{-8}$ |
| (morpholino)O—NSO$_2$—PHE—HIS—CHSTA—NHCH$_2$CH(CH$_3$)CH$_2$CH$_3$ | $4.8 \times 10^{-9}$ |
| (morpholino)O—NSO$_2$—PHE—NH—CH(CO$_2$Et)—CO—CHSTA—NHCH$_2$CH(CH$_3$)CH$_2$CH$_3$ | $3.2 \times 10^{-8}$ |
| (morpholino)O—NSO$_2$—PHE—HIS—CYSTA—NHCH$_2$CH$_2$—N(morpholino) | $5.0 \times 10^{-9}$ |
| (morpholino)O—NSO$_2$—NAPHTHYLALA—HIS—STA—NHCH$_2$CH(CH$_3$)CH$_2$CH$_3$ | $3.0 \times 10^{-9}$ |
| (piperazino)HN—NSO$_2$—PHE—HIS—STA—NHCH$_2$CH(CH$_3$)CH$_2$CH$_3$ | $3.5 \times 10^{-7}$ |
| CH$_3$N(piperazino)—NSO$_2$—PHE—HIS—STA—NHCH$_2$CH(CH$_3$)CH$_2$CH$_3$ | $1.5 \times 10^{-7}$ |
| (morpholino)O—NSO$_2$—PHE—NIA—STA—NHCH$_2$CH(CH$_3$)CH$_2$CH$_3$ | $2.5 \times 10^{-8}$ |
| Me$_2$NSO$_2$—PHE—PGY—STA—NHCH$_2$CH$_2$—N(morpholino) | $3.2 \times 10^{-7}$ |
| Me$_2$NSO$_2$—PHE—PGY—STA—NHCH$_2$CH(CH$_3$)CH$_2$CH$_3$ | $3.4 \times 10^{-8}$ |
| Me$_2$NSO$_2$—PHE—HIS—STA—NHCH$_2$CH$_2$—N(morpholino) | $\approx 9.0 \times 10^{-7}$ |
| Me$_2$NSO$_2$—PHE—ALG—STA—NHCH$_2$CH$_2$—N(morpholino) | $1.6 \times 10^{-7}$ |

TABLE 2-continued

| Compound | IC$_{50}$ (M) |
|---|---|
| O(morph)-NSO$_2$-PHE-NH-CH(CO$_2$Me)-CO-STA-NHCH$_2$CH$_2$-N(morph)O | $1.3 \times 10^{-7}$ |
| O(morph)-NSO$_2$-PHE-HIS-STA-NHCH$_2$CH$_2$-N(morph)O | $3.0 \times 10^{-7}$ |
| Z-N(piperaz)N-CO-PHE-HIS-STA-NHCH$_2$CH(CH$_3$)CH$_2$CH$_3$ | $1.4 \times 10^{-7}$ |
| O(morph)-NSO$_2$-PHE-LYS(CO$_2$CH$_2$Ph)-DFSTA-NHCH$_2$CH$_2$-N(morph)O | $4.5 \times 10^{-8}$ |
| O(morph)-NSO$_2$-PHE-LYS(COCH$_3$)-DFSTA-NHCH$_2$CH$_2$-N(morph)O | $3.0 \times 10^{-6}$ |
| O(morph)-NSO$_2$-PHE-ALG-DFSTA-NHCH$_2$CH$_2$-N(morph)O | $1.1 \times 10^{-8}$ |
| O(morph)-NSO$_2$-PHE-NH-CH(CO$_2$Me)-CO-DFSTA-NHCH$_2$CH$_2$-N(morph)O | $4.0 \times 10^{-8}$ |
| O(morph)-NSO$_2$-PHE-HIS-DFKCYS-NHCH$_2$CH$_2$-N(morph)O | $1.0 \times 10^{-9}$ |
| O(morph)-NSO$_2$-PHE-ALG-DFKSTA-NHCH$_2$CH$_2$-N(morph)O | $6.0 \times 10^{-9}$ |
| O(morph)-NSO$_2$-PHE-NH-CH(CO$_2$Me)-CO-DFKSTA-NHCH$_2$CH$_2$-N(morph)O | $1.5 \times 10^{-8}$ |
| O(morph)-NSO$_2$-PHE-ALG-DFCYS-NHCH$_2$CH$_2$-N(morph)O | $7.0 \times 10^{-10}$ |
| O(morph)-NSO$_2$-PHE-ALG-DFKCYS-NHCH$_2$CH$_2$-N(morph)O | $9.0 \times 10^{-10}$ |

As can be seen from the above table, the compounds of the present invention have a significant effect on the activity of renin and thus are useful for the treatment of hypertension, hyperaldosteronism, and congestive heart failure.

For preparing pharmaceutical compositions for the compounds described by this invention, inert, pharmaceutically acceptable carriers can be either solid or liquid. Solid form preparations includes powders, tablets, dispersible granules, capsules, cachets, and suppositories. A solid carrier can be one or more substances which may also act as diluents, flavoring agents, solubilizers, lubricants, suspending agents, binders, or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powder and tablets preferably contain from 5 to 10 to about 70 percent of the active ingredient. Suitable solid carriers are magnesium carbonate, magnesium stearate, talc, sugar, tragacanth, methylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

The compound of the present invention may be administered orally, buccally, parenterally, by inhalation spray, rectally, or topically in dosage unit formulations containing conventional nontoxic pharmaceutically acceptable carriers, adjuvants and vehicles as desired. The term parenteral as used herein includes subcutaneous injections, intravenous, intramuscular, intrasternal injection, or infusion techniques.

For preparing suppositories, a low melting wax such as a mixture of fatty acid glycerides or cocoa butter is first melted, and the active ingredient is dispersed homogeneously therein by stirring. The molten homogeneous mixture is then poured into convenient sized molds, allowed to cool, and thereby solidify.

Liquid form preparations include solutions, suspensions, and emulsions. As an example may be mentioned water or water/propylene glycol solutions for parenteral injection. Liquid preparations can also be formulated in solution in aqueous polyethyleneglycol solution. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dosage form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like, as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably 5 to 100 mg according to the particular application and the potency of the active ingredient. The compositions can, if desired, also contain other compatible therapeutic agents.

In therapeutic use as renin inhibitors, the mammalian dosage range for a 70 kg subject is from 1 to 1500 mg/kg of body weight per day or preferably 25 to 750 mg/kg of body weight per day optionally in divided portions. The dosages, however, may be varied depending upon the requirements of the patient, the severity of the condition being treated and the compound being employed. Determination of the proper dosage for a particular situation is within the skill of the art. Generally, treatment is initiated with small dosages which are less than the optimum dose of the compound. Thereafter the dosage is increased by small increments until the optimum effect under the circumstances is reached. For convenience, the total daily dosage may be divided and administered in portions during the day if desired.

The following examples are provided to enable one skilled in the art to practice the present invention. These examples are not intended in any way to limit the scope of the invention but are illustrative thereof.

EXAMPLE 1

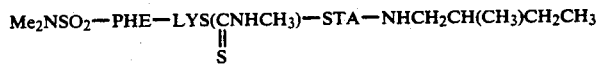

A mixture of Me$_2$NSO$_2$-PHE (0.55 g), DCC (0.42 g), HOBT.H$_2$O (0.27 g), and DMF (10 ml) was stirred at 25° for ten minutes. The resulting suspension was treated with a solution of LYS(CSNHCH$_3$)-STA-NHCH$_2$CH(CH$_3$)CH$_2$CH$_3$ (0.89 g) in DMF (10 ml). The reaction mixture was stirred for twenty-four hours at 25° and filtered. The filtrate was concentrated under a vacuum and the residue was dissolved in CH$_2$CL$_2$ (60 ml). This solution was washed with 5% aqueous Na$_2$CP$_3$, dried over MgSO$_4$, and evaporated. The major product was isolated by flash chromatography on silica gel, eluting with CHCl$_3$-MeOH (99:1). Purified product was evaporated from CH$_2$Cl$_2$ solution to give a crisp foam. MS (FAB) 700 (m+1). (FAB is fast atom bombardment.)

The following compounds were obtained in an analogous manner:
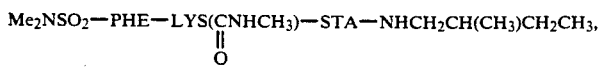
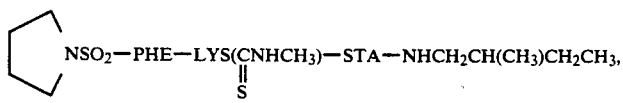
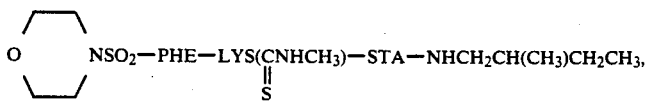
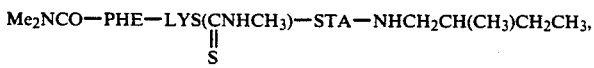
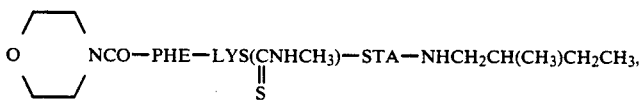
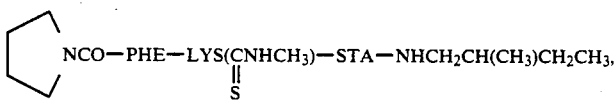
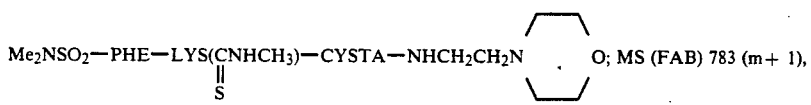
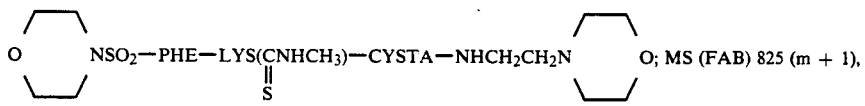
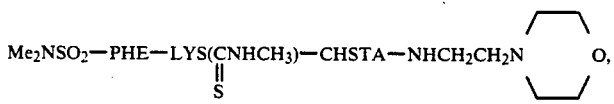
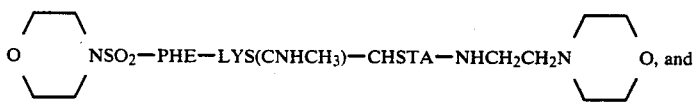
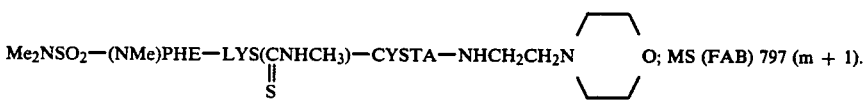
EXAMPLE 2
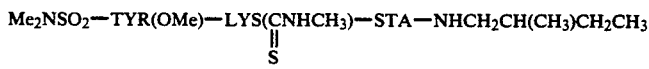
Substitution of Me$_2$NSO$_2$-TYR(OMe) for Me$_2$NSO$_2$-PHE in Example 1 affords this analogous product. MS (FAB) 730 (m+1).
The following compounds are obtained in an analogous manner:
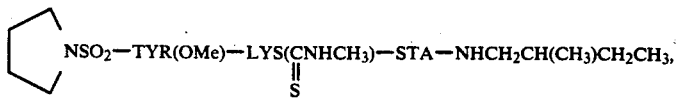

-continued

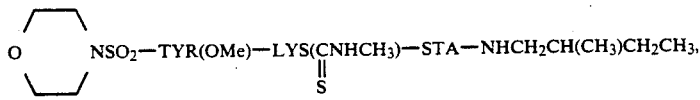

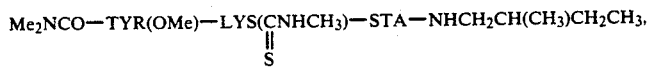

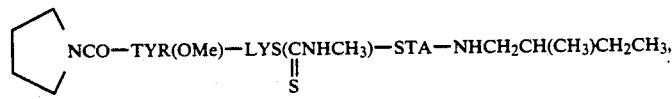

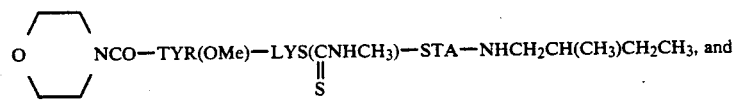

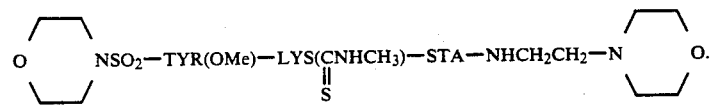

EXAMPLE 3

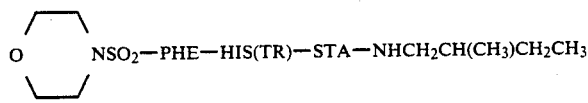

A mixture of morpholinosulfamyl-PHE (0.63 g), DCC (0.42 g), HOBT.H₂O (0.27 g), and DMF (10 ml) was stirred at 25° for ten minutes. The resulting slurry was treated with a solution of HIS(TR)-STA-NHCH₂CH(CH₃)CH₂CH₃ (1.25 g) in DMF (5 ml). After stirring twenty-four hours at 25° the reaction mixture was filtered and concentrated under vacuum. The residue was dissolved in CH₂Cl₂ (75 ml) and this solution was washed with 5% aqueous Na₂CO₃ (25 ml), dried over MgSO₄, and evaporated. The major product was isolated by flash chromatography on silica gel, eluting with CHCl₃-MeOH (99:1) to give a crisp foam (1.3 g) upon evaporation from CH₂Cl₂ solution. TLC R$_f$=0.57 (silica gel, CHCl₃-MeOH (9:1)).

The following compounds are obtained in an analogous manner:

Me₂NSO₂—PHE—HIS(TR)—STA—NHCH₂CH(CH₃)CH₂CH₃,

Me₂NSO₂—TYR(OMe)—HIS(TR)—STA—NHCH₂CH(CH₃)CH₂CH₃,

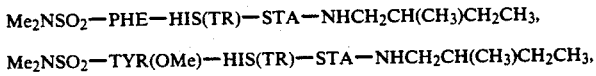

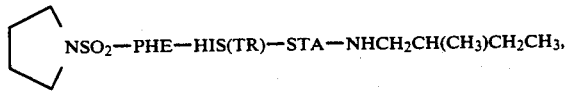

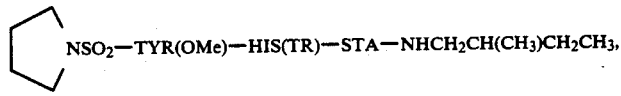

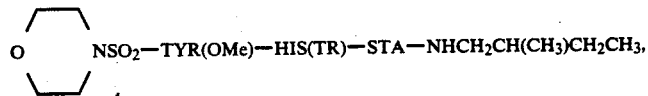

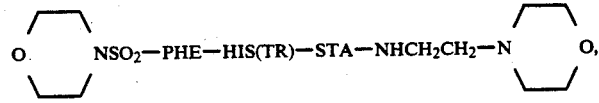

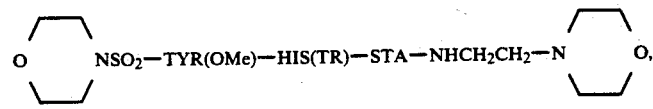

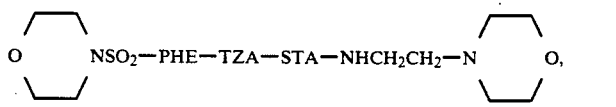

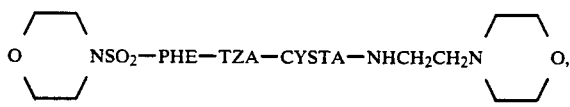

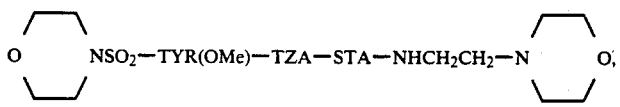

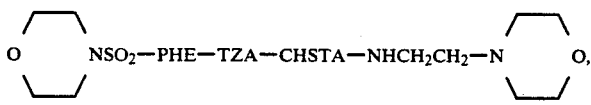

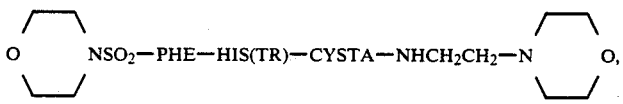

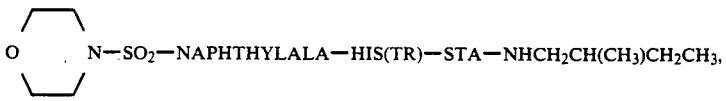

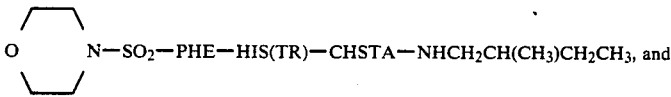

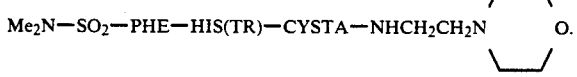

EXAMPLE 4

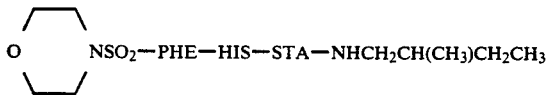

A solution of trityl-protected tripeptide from Example 3 above (1.3 g) in 80% acetic acid (10 ml) was heated in a steam bath until the solution temperature remained above 90° for three minutes. The hot solution was diluted with water (15 ml) and the resulting precipitate was removed by filtration. The aqueous filtrate was evaporated at reduced pressure and the residue was partitioned between CH$_2$Cl$_2$ (75 ml) and 10% aqueous Na$_2$CO$_3$ (30 ml). The organic layer was dried over MgSO$_4$ and evaporated to a crisp foam (0.87 g). MS (FAB) 678 (m+1).

The following compounds were obtained in an analogous manner:

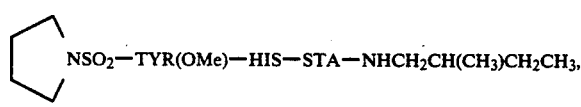

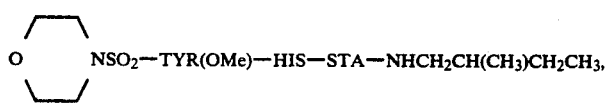

-continued

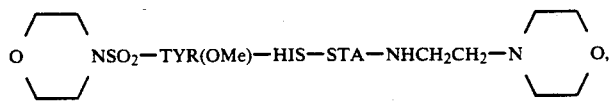

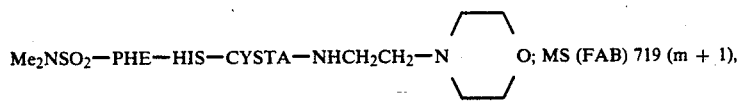
Me₂NSO₂—PHE—HIS—CYSTA—NHCH₂CH₂—N⟨ ⟩O; MS (FAB) 719 (m + 1),

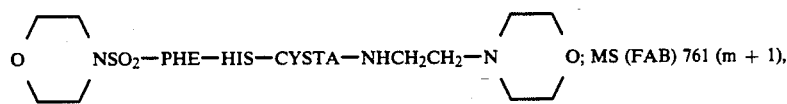

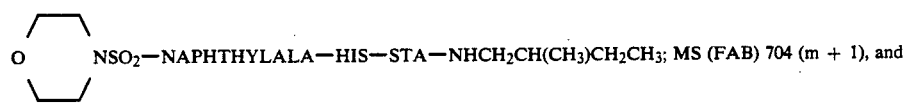

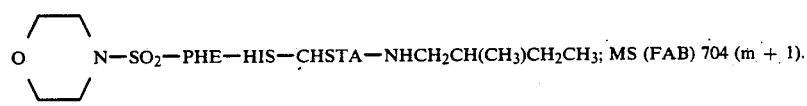

EXAMPLE 5

Me₂NSO₂-PHE-HIS-STA-NHCH₂CH(CH₃)CH₂CH₃

Substitution of Me₂NSO₂-PHE in Example 3 give the analogous trityl-protected tripeptide which was deprotected as in Example 4 to afford Me₂NSO₂-PHG-HIS-STA-NHCH₂CH(CH₃)CH₂CH₃. MS (FAB) 636 (m+1).

EXAMPLE 6

Substitution of pyrrolidinosulfamyl-PHE in Example 3 gives the analogous trityl-protected tripeptide which was deprotected as in Example 4 to afford pyrrolidinosulfamyl-PHE-HIS-STA-NHCH₂CH(CH₃)CH₂CH₃. MS (FAB) 662 (m+1).

EXAMPLE 7

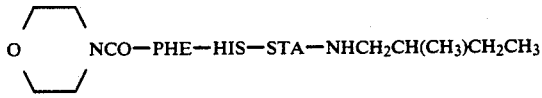

Substitution of morpholinocarbamyl-PHE in Example 3 gives the analogous trityl-protected tripeptide which was deprotected as in Example 4 to afford morpholinocarbamyl-PHE-HIS-STA-NHCH₂CH(CH₃)CH₂CH₃. MS (FAB) 642 (m+1).

The following compounds are obtained in an analogous manner:

Me₂NCO—PHE—HIS—STA—NHCH₂CH(CH₃)CH₂CH₃,

Me₂NCO—TYR(OMe)—HIS—STA—NHCH₂CH(CH₃)CH₂CH₃,

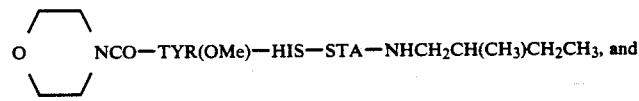

EXAMPLE 8

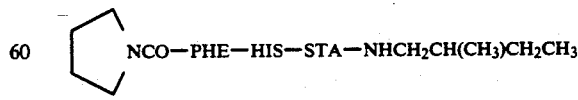

Substitution of pyrrolidinocarbamyl-PHE in Example 3 gives the analogous trityl-protected tripeptide which was deprotected as in Example 4 to afford pyrrolidinocarbamyl-PHE-HIS-STA-NHCH₂CH(CH₃)CH₂CH₃. MS (FAB) 626 (m+1).

EXAMPLE 9

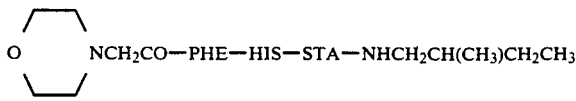

Substitution of morpholinoacetyle-PHE in Example 3 gives the analogous trityl-protected tripeptide which was deprotected as in Example 4 to afford morpholinoacetyl-PHE-HIS-STA-NHCH₂CH(CH₃)CH₂CH₃. MS (FAB) 656 (m+1).

The following compounds are obtained in an analogous manner:

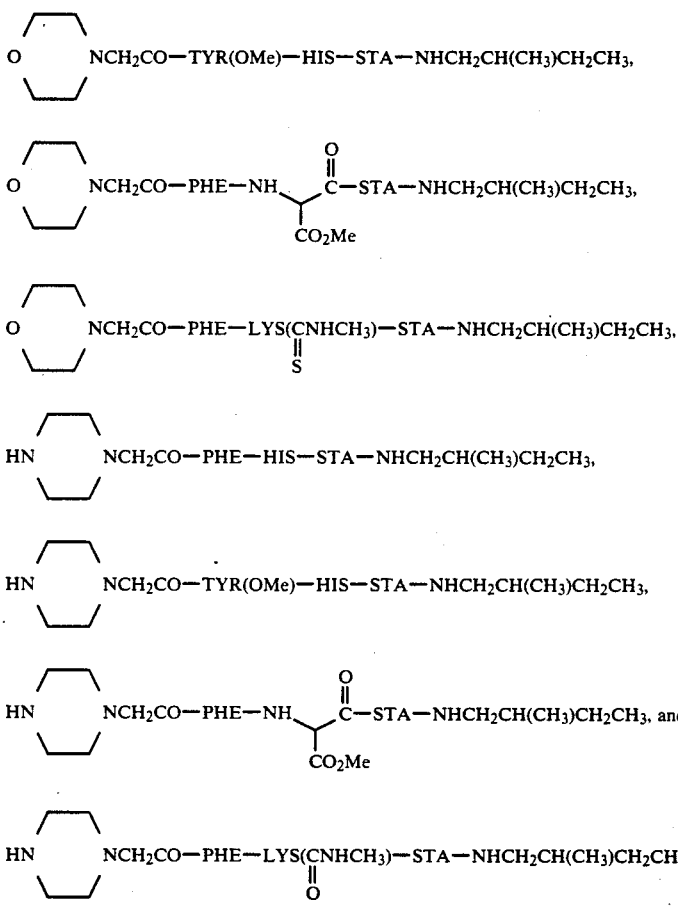

EXAMPLE 10

Me₂NSO₂-PHE-HNCH(CO₂Me)CO-STA-NHCH₂CH(CH₃)CH₂CH₃

Me₂NSO₂-PHE (1.13 g) and HOBT.H₂O (0.58 g) were dissolved in a mixture of CH₂Cl₂ (100 ml) and DMF (8 ml). After cooling the mixture to 0°, a solution of H₂NCH(CO₂Me)CO-STA-NHCH₂CH(CH₃)CH₂CH₃ (1.49 g) in CH₂Cl₂ (20 ml) was added, followed by addition of DCC (0.88 g). The mixture was stirred at 0° for several hours, then allowed to warm to 23° overnight. The resulting suspension was filtered and the filtrate was evaporated to an oil. This oil was dissolved in ethyl acetate and refiltered. The filtrate was washed consecutively with 1 N citric acid, brine, saturated aqueous NaHCO₃, and brine. The organic phase was then dried over MgSO₄ and evaporated to a waxy solid (2.85 g). Chromatography on silica gel, eluting with CHCl₃-ethyl acetate (1:1) affords the major project as a crisp foam which was suspended in ethyl ether and evaporated, giving a semicrystalline solid (1.95 g). Calcd. for $C_{28}H_{47}N_5O_8S \cdot 0.03CHCl_3 \cdot 0.25H_2O$: C, 54.14; H, 7.70; N, 11.26; Cl, 0.51; H₂O, 0.72; S, 5.16.

Found C, 54.22; H, 7.70; N, 11.27; Cl, 0.52; H₂O, 0.98; S, 5.55.

The following compounds were obtained in an analogous manner:

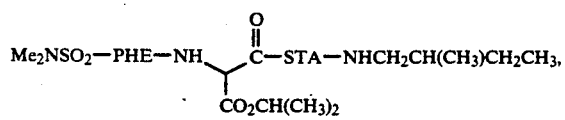

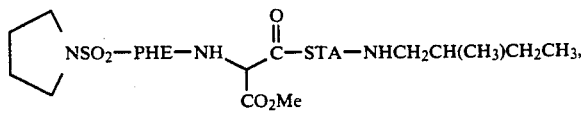
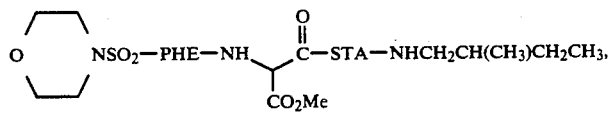
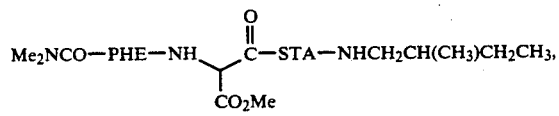
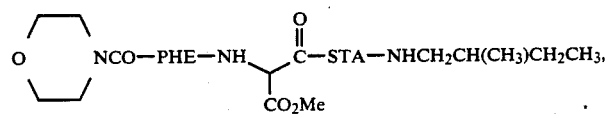
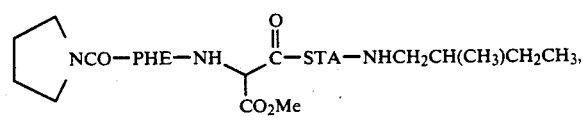
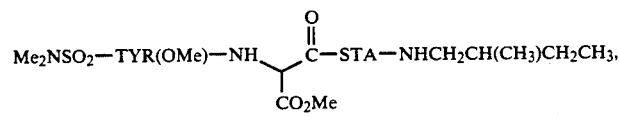
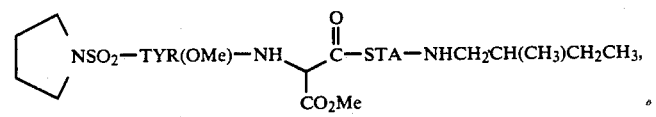
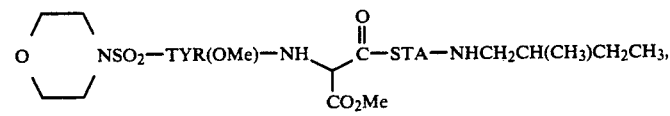
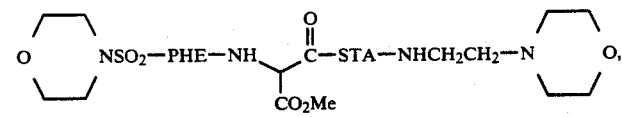
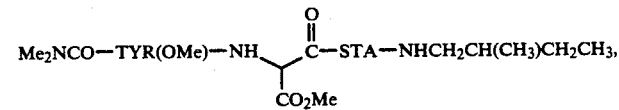
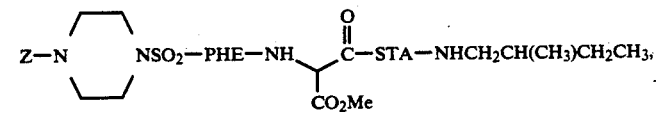
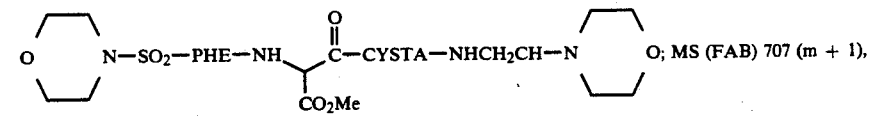

-continued

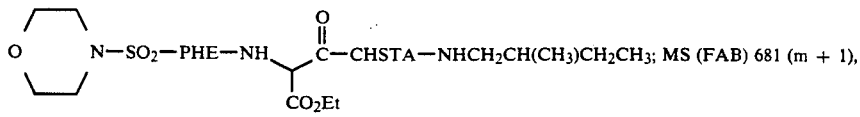

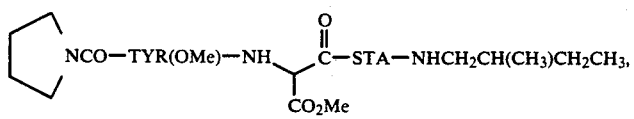

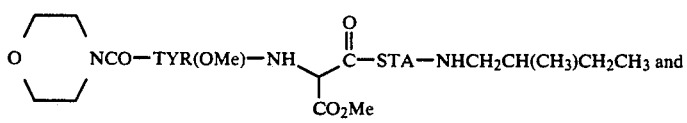

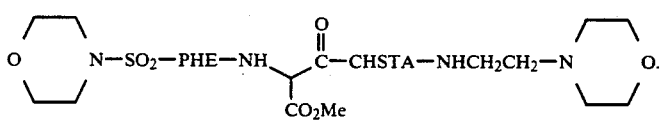

EXAMPLE 11

Me$_2$NSO$_2$-PHE-ALG-STA-NHCH$_2$CH(CH$_3$)CH$_2$CH$_3$

A solution of BOC-ALG-STA-NHCH$_2$CH(CH$_3$)CH$_2$CH3 (2.09 g) in a mixture of trifluoroacetic acid (10 mL) and CH$_2$Cl$_2$ (20 mL) was stirred for 2 hours at room temperature. The solution was concentrated, taken up in CH$_2$Cl$_2$, and re-concentrated. The residue was taken up in CH$_2$Cl$_2$ and treated for several minutes with HCl(g). The solution was concentrated to yield an oil which was taken up in 30 ml of DMF and treated with (iPr)$_2$NEt until basic. The solution was treated with HOBT.H$_2$O (0.67 g) and cooled in an ice bath. The mixture was treated with Me$_2$NSO$_2$-PHE (1.29 g) and DCC (1.04 g), stirring in an ice bath for 2 hours and then overnight at room temperature. After filtering, the filtrate was concentrated under high vacuum. The residue was taken up in EtOAc and washed with 1N citric acid, brine, saturated NaHCO$_3$, and brine. After drying over Na$_2$SO$_4$, the solution was concentrated to yield a tan solid which was purified by flash chromatography (EtOAc) to yield 1.26 g (44.7%) of a foam. MS (FAB) 596 (m+1).

The following compounds were prepared in an analogous manner:

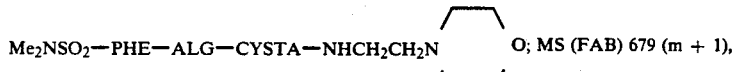

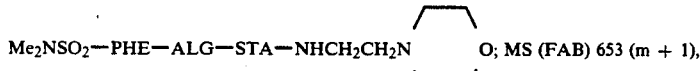

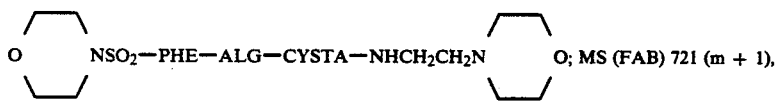

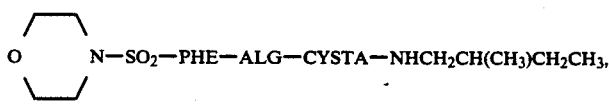

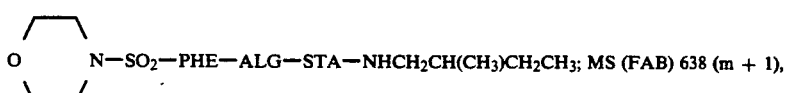

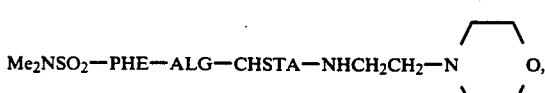

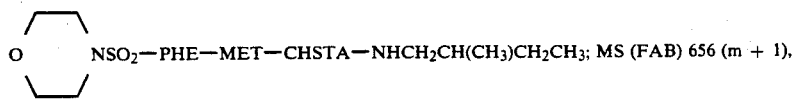

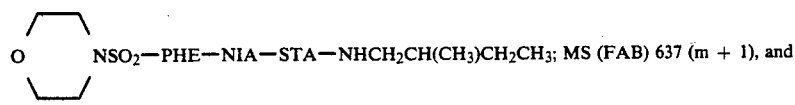

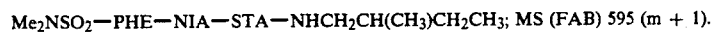

Me₂NSO₂—PHE—NIA—STA—NHCH₂CH(CH₃)CH₂CH₃; MS (FAB) 595 (m + 1).

EXAMPLE 12

Me₂NSO₂-PHE-PGY-STA-NHCH₂CH(CH₃)CH₂CH₃

A solution of the corresponding ALG adduct from Example 11 was reduced by catalytic hydrogenation in methanol, using 5% Pd on carbon catalyst. MS (FAB) 598 (m+1).

The following compounds were prepared in an analogous manner:

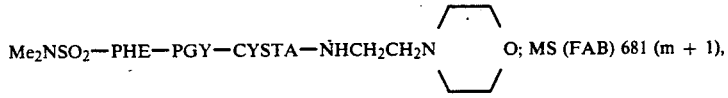

Me₂NSO₂—PHE—PGY—CYSTA—NHCH₂CH(CH₃)CH₂CH₃; MS (FAB) 638 (m + 1),

Me₂NSO₂—PHE—PGY—CHSTA—NCHCH₂CH(CH₃)CH₂CH₃,

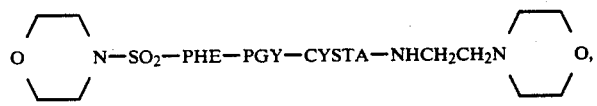

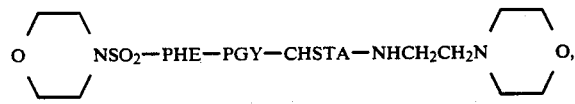

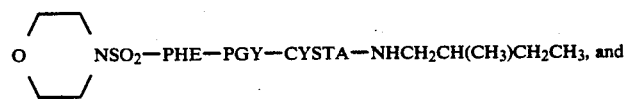

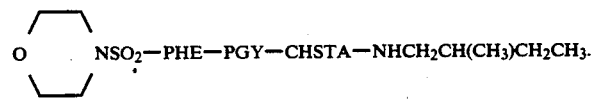

EXAMPLE 13

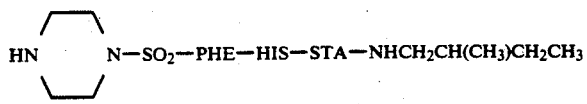

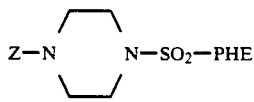

(1.3 g) was coupled to HIS(TR)-STA-NHCH$_2$CH(CH$_3$)CH$_2$CH$_3$ (1.9 g) according to the method of Example 3. The resulting product (2.5 g) was dissolved in methanol (75 mL), treated with 20% Pd on carbon (0.5 g) and placed under an atmosphere of hydrogen, stirring vigorously for 2 hours. Filtration and evaporation of the filtrate gave

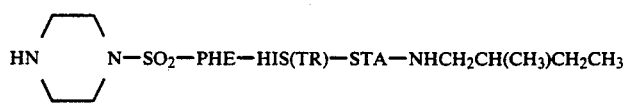

which was treated with 80% acetic acid according to the method of Example 4 to give the desired product. MS (FAB) 677 (m+1).

The following compounds were prepared in an analogous manner.

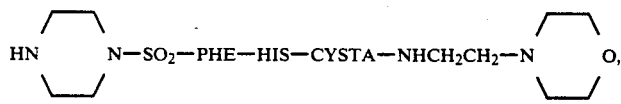

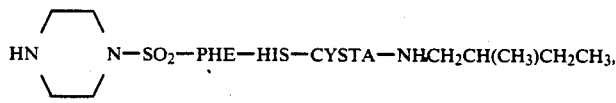

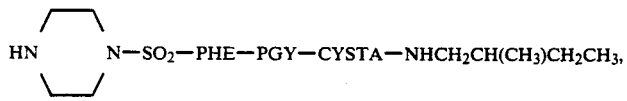

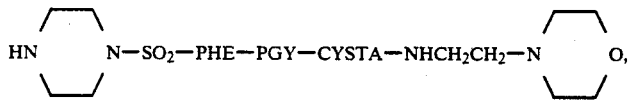

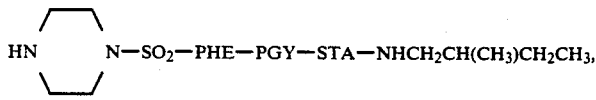

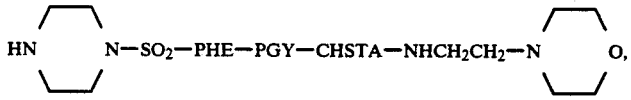

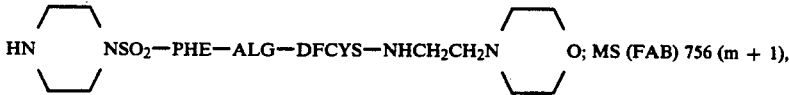

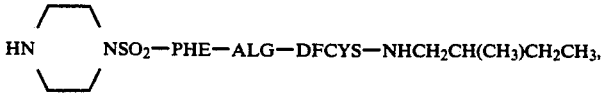

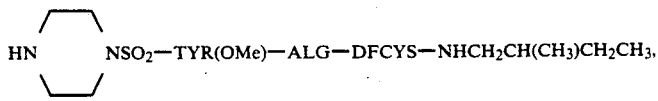

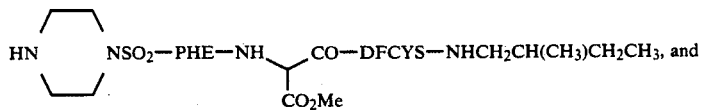

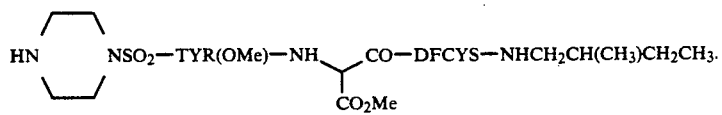

EXAMPLE 14

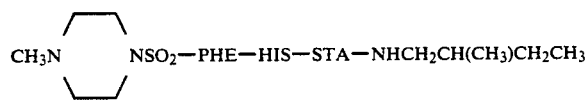

A solution of

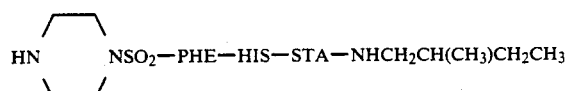

(740 mg) in ethanol (10 mL) was treated with 37% aqueous formaldehyde (0.5 mL) and formic acid (5 mL). The resulting solution was heated at reflux for 3 hours. After cooling the reaction mixture was evaporated and the residue was partitioned between ethyl acetate and 10% $K_2CO_3$. The organic layer was dried over $MgSO_4$, evaporated and chromatographed to give the N-methylated product (690 mg). MS (FAB) 691 (m+1).

The following compounds were prepared in an analogous manner:

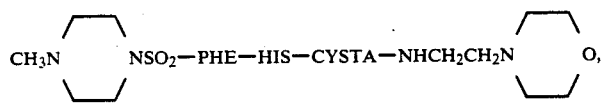

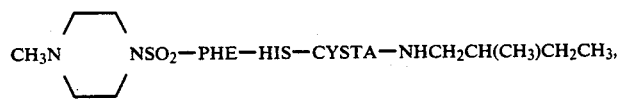

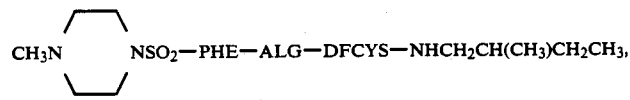

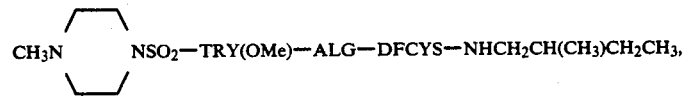

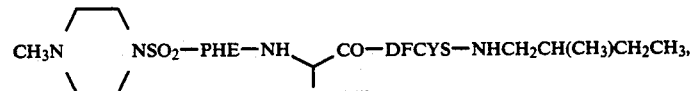

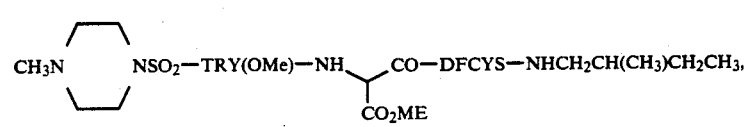

-continued

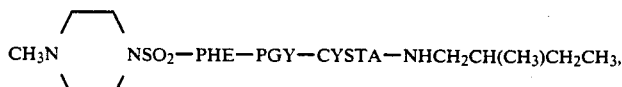

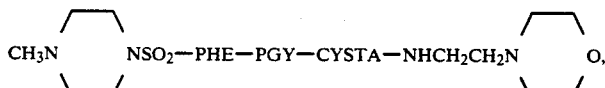

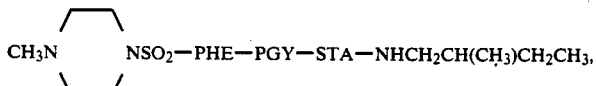

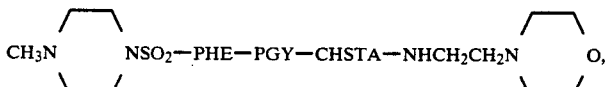

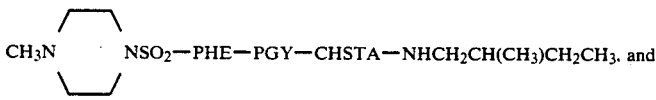

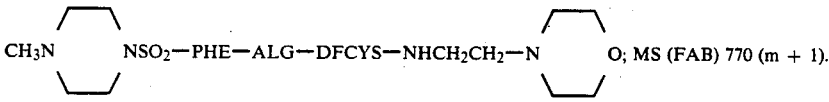

EXAMPLE 15

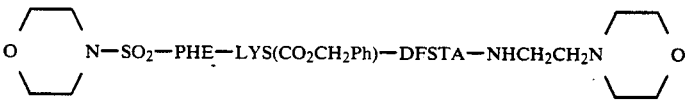

To N-morpholinosulfamyl-L-phenylalanine (0.80 g, 2.55 mmol) and 1-hydroxybenzotriazole hydrate (346 mg, 2.56 mmol) in DMF (30 μl) at 0° C. was added dicyclohexylcarbodiimide (528 mg, 2.56 mmol) in DMF (5 ml) portionwise. After complete addition LYS(CO₂CH₂Ph)—DFSTA—NHCH₂CH₂N⟨O⟩

(1.50 g, 2.56 mmol) in DMF (15 ml) was added to the solution and the reaction stirred for 1 hour at 0° C. before allowing to warm to room temperature. After stirring for about 16 hours, the precipitated dicyclohexylurea was removed by filtration and the DMF evaporated under high vacuum. The resulting residue was taken up in ethyl acetate and washed with 1M aqueous sodium hydroxide solution, followed by brine. After drying (Na₂SO₄), the solvent was removed under reduced pressure. Column chromatography on silica gel employing 5–10% methanol/chloroform afforded the desired product as a white foam (2.0 g, 85%) MS (FAB) 882 (m+1).

The following compounds were prepared in an analogous manner:

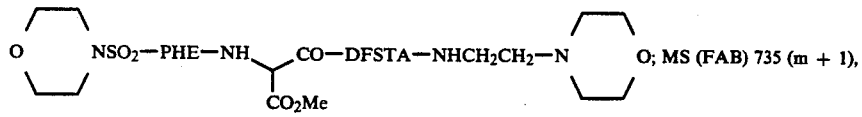

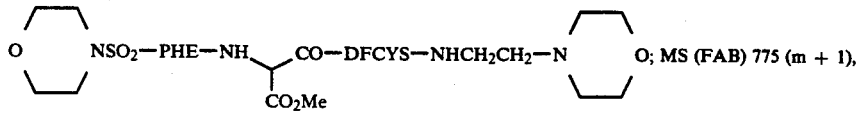

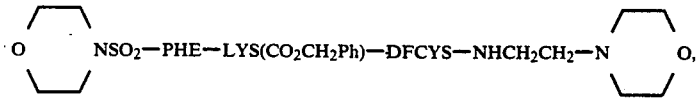

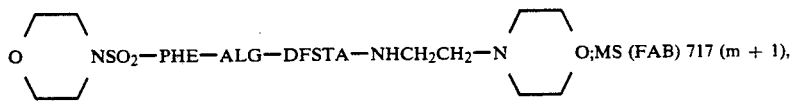
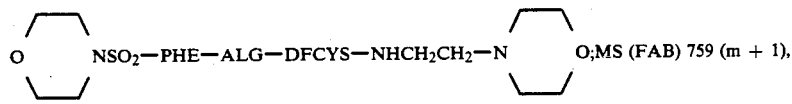
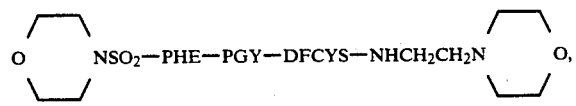
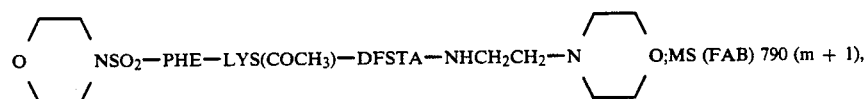
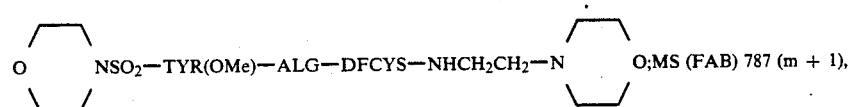
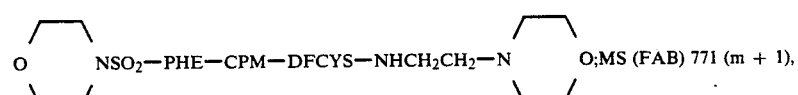
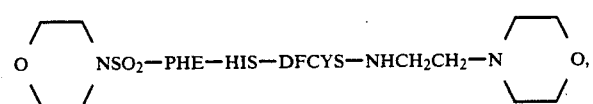
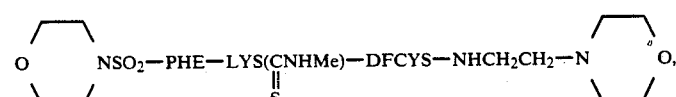
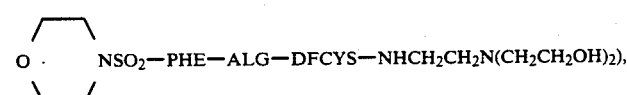
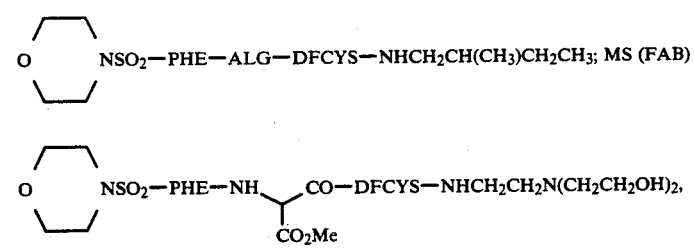
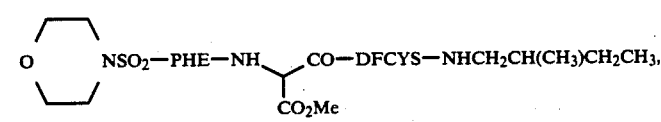
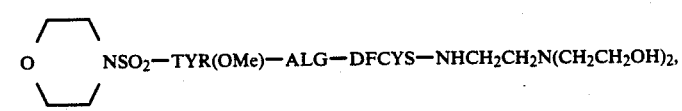

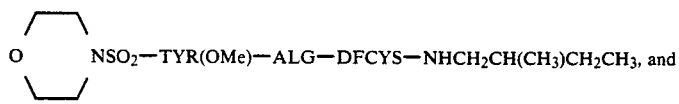

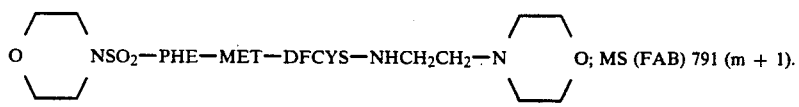

EXAMPLE 16

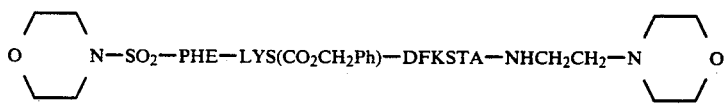

To oxalyl chloride (64.4 μl, 0.74 mmol) in dry dichloromethane (5 ml) at −70° C. was added dry distilled dimethylsulfoxide (106 μl, 1.50 mmol) and the solution stirred for 10 minutes. The product from Example 15 (0.50 g, 0.57 mmol) in dichloromethene (5ml) was then added and the resulting solution stirred at between −60° and −50° C. for 30 minutes. The reaction was then allowed to reach −30° C. and stirred for 30 minutes before precooling to −70° C. Dry triethylamine (394 μl, 2.84 mmol) was added and the reaction was allowed to warm to room temperature slowly. After dilution with dichloromethane, the solution was washed with a saturated aqueous solution of sodium bicarbonate. Drying ($Na_2SO_4$), filtration and evaporation of the solvent afforded a crude residue. Column chromatography afforded the desired product of white foam (378 mg, 75.6%). MS (FAB) 880 (m+1).

The following compounds were prepared in an analogous manner:

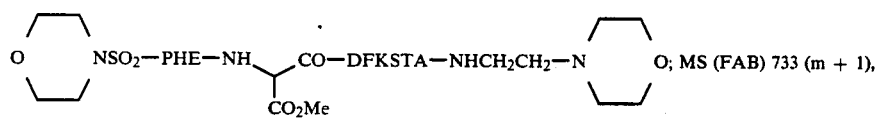

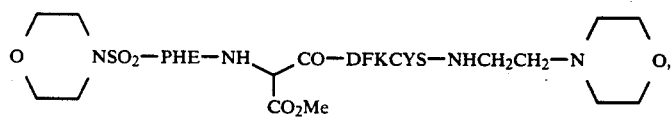

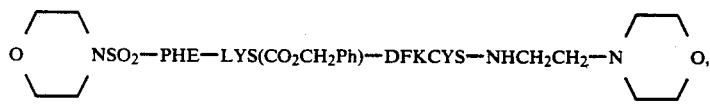

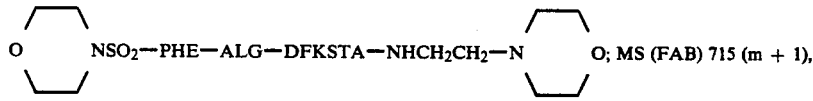

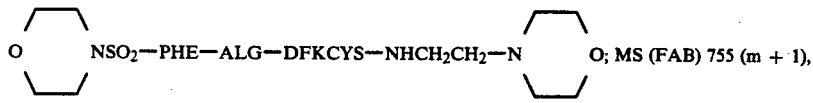

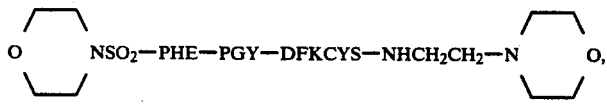

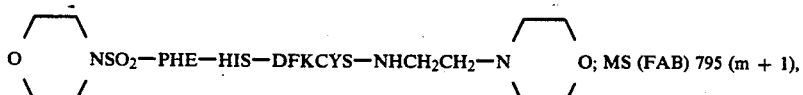

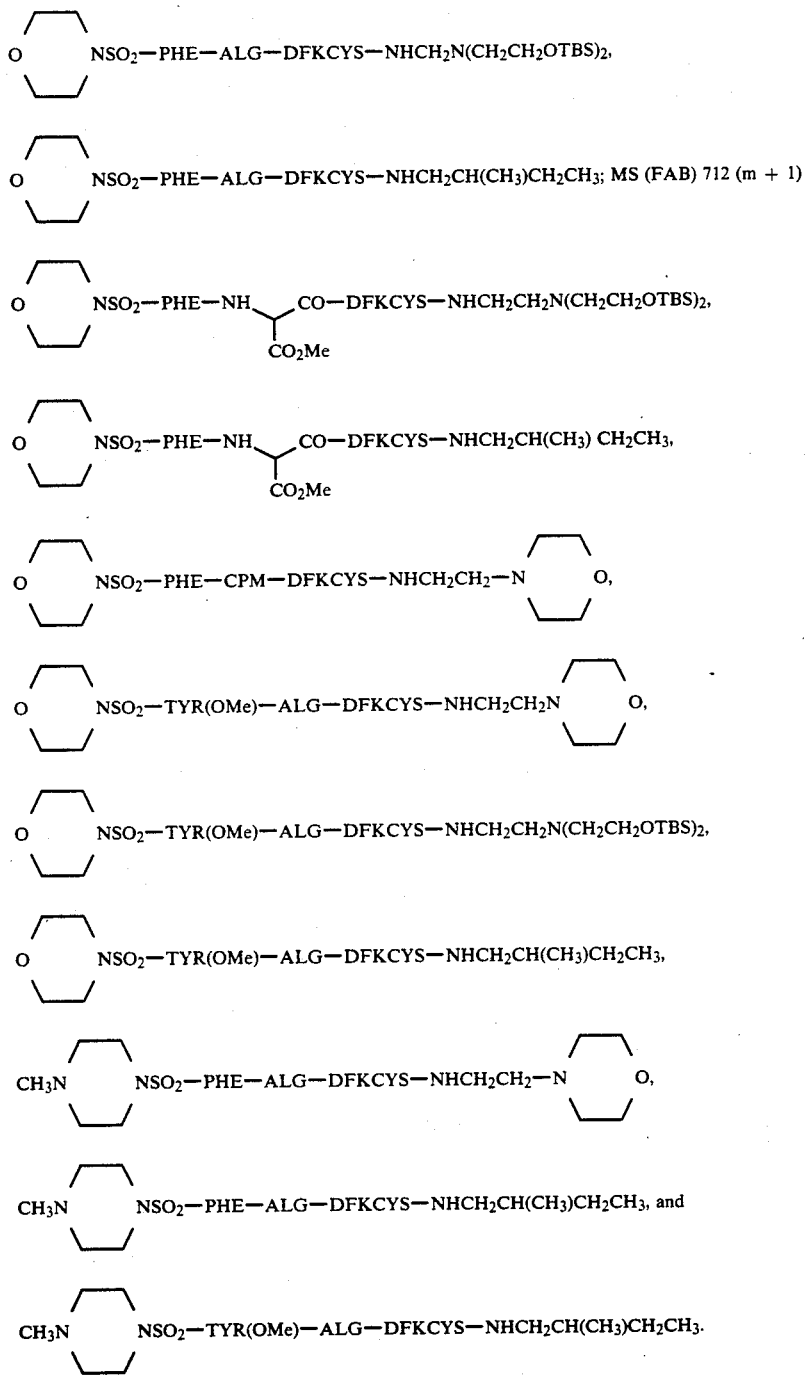

INTERMEDIATES FOR EXAMPLES 1-16

BOC-DFCYS

Activated Zn dust (9.2 g) was suspended in dry THF (300 ml) under $N_2$. A crystal of iodine was added and the mixture was heated to reflux. Ethyl bromodifluoroacetate (0.1 ml) was added to initiate the Reformatsky reaction then a mixture of S-N-BOC-cyclohexylalanal (18 g), Ethyl bromodifluoroacetate (13.6 ml) and THF (100 ml) was added over seven minutes. The reaction was refluxed for 30 minutes further, cooled to 25° C. and partitioned between ethyl acetate (400 ml) and 1M $KHSO_4$ (100 ml). The organic layer was washed with water and saturated aqueous NaCl. It was then dried over $MgSO_4$ and chromatographed on silica gel (pet. ether - ethyl acetate 85:15) to give the desired product as an oil. Addition of hexane causes precipitation of the major diastereomer, S,R-BOC-DFCYS-OEt (4.6 g), as a white solid. This material was dissolved in THF (30 ml), treated with 1.1 eq. 1 N NaOH, and stirred at 25° C. for four hours. Acidification with citric acid and extraction into ethyl acetate afforded S,R-BOC-DFCYS (4.8 g) upon drying ($MgSO_4$) and evaporation. MS (FAB) 352 (m+1).

BOC-STA-NHCH₂CH(CH₃)CH₂CH₃

BOC-STA (27.53 g, 0.1 mole, US Patent 4,397,786) and HOBT.H₂O (14.2 g, 0.105 mole) were dissolved in 40 ml DMF. 25 300 ml CH₂Cl₂ was added, and the mixture was cooled to 0°. A solution of DCC (21.66 g, 0.105 mole) in 50 ml CH₂Cl₂ was added, followed by S-2-methylbutylamine (12 ml, 0.1 mole). After stirring at 0° for two hours, the mixture was allowed to warm to 25° over 1.5 hours. The mixture was filtered, and the solvent was removed in vacuo. The residue was dissolved in EtOAc, which was washed with 1 N citric acid, brine, saturated NaHCO₃ solution, and brine. The organic phase was dried over MgSO₄, filtered, and stripped to a gum, 36.90 g. The gum was dissolved in Et₂O and treated with charcoal to remove colored impurities. The suspension was filtered and stripped to a gum, 35.2 g, which was suitable for use in the following procedure without further purification.

The following compounds are obtained in an analogous manner:

BOC—CYSTA—NHCH₂CH(CH₃)CH₂CH₃,

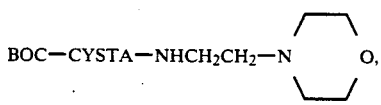
BOC—CYSTA—NHCH₂CH₂—N  O,

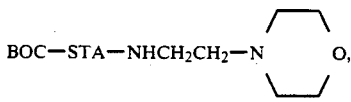
BOC—STA—NHCH₂CH₂—N  O,

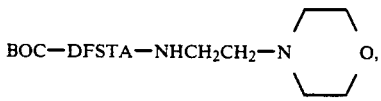
BOC—DFSTA—NHCH₂CH₂—N  O,

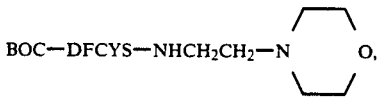
BOC—DFCYS—NHCH₂CH₂—N  O,

BOC—DFCYS—NHCH₂CH₂N(CH₂CH₂OH)₂,

BOC—DFCYS—NHCH₂CH(CH₃)CH₂CH₃,

BOC—DFSTA—NHCH₂CH(CH₃)CH₂CH₃,

BOC—CHSTA—NHCH₂CH(CH₃)CH₂CH₃, and

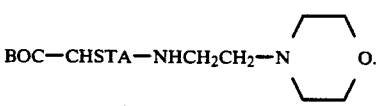
BOC—CHSTA—NHCH₂CH₂—N  O.

STA-NHCH₂CH(CH₃)CH₂CH₃

A solution of BOX-STA-NHCH₂CH(CH₃)CH₂CH₃ (15.4 g) in CH₂Cl₂ (300 ml) was treated with freshly prepared methanolic HCl (100 ml) and stirred 75 minutes at 25°. The resulting solution was evaporated and the residue partitioned between diethyl ether and 10% Na₂CO₃ (aq). The organic layer was dried over MgSO₄ and evaporated to give 9.9 g of a tacky, colorless solid which was suitable for use without further purification.

The following compounds are obtained in an analogous manner:
DFSTA-NHCH₂CH(CH₃)CH₂CH₃

DFCYS-NHCH₂CH(CH₃)CH₂CH₃,
CYSTA-NHCH₂CH(CH₃)CH₂CH₃, and
CHSTA-NHCH₂CH(CH₃)CH₂CH₃.

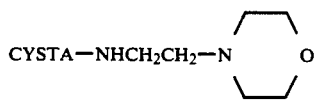
CYSTA—NHCH₂CH₂—N  O

A solution of

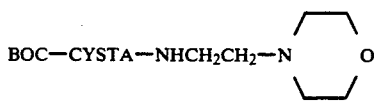
BOC—CYSTA—NHCH₂CH₂—N  O (10 g) in CH₂Cl₂ (250 mL) was treated with methanolic HCl (250 mL) and stirred for 2 hours at 25°. The resulting solution was evaporated and the residue was treated with a saturated solution of ammonia in CH₂Cl₂ (300 mL). After 10 minutes of vigorous stirring, NH₄Cl was removed by filtration and the filtrate was evaporated to give the product as a solid.

The following compounds are prepared in an analogous manner:

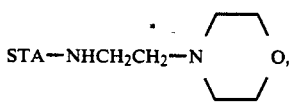
STA—NHCH₂CH₂—N  O,

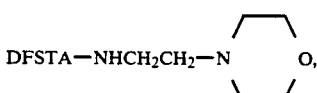
DFSTA—NHCH₂CH₂—N  O,

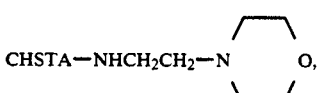
CHSTA—NHCH₂CH₂—N  O,

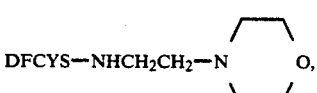
DFCYS—NHCH₂CH₂—N  O,

DFCYS—NHCH₂CH₂N(CH₂CH₂OH)₂.

Me₂NSO₂-PHE

A solution of PHE (3.3 g) in 1 N NaOH (20 ml) was treated with a solution of N,N-dimethylsulfamyl chloride (2.3 ml) in THF (20 ml) and stirred vigorously at 25° for three hours. The reaction mixture was then treated with additional 1 N NaOH (20 ml) and N,N-dimethylsulfamyl chloride (2.3 ml) and stirred 3 hours further at 25°. Finally, 1 N NaOH (20 ml) and diethyl ether (80 ml) were added. The mixture was shaken and the aqueous layer was separated and acidified to pH 1 by addition of 1 N HCl (25 ml). Product was extracted into ethyl acetate, the solution was dried over MgSO₄, and evaporated to give a gum which slowly solidifies (4.0 g). NMR δ(CDCl₃) 8.7 (br, 1H), 7.3 (m, 5H), 5.0 (d, 1H), 4.3 (m, 1H), 3.1 (AB of ABX, 2H), 2.6 (S, 6H).

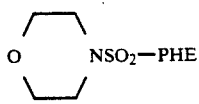

Prepared as above, substituting morpholinosulfamyl chloride (prepared according to the method of R. Wegler and K. Bodenbenner, *Annallen der Chemie*, 624, 25 (1959)) for N,N-dimethylsulfamyl chloride. Product is a solid, mp 151°–153° C.

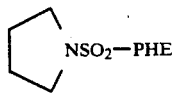

Prepared as above, substituting pyrrolidinosulfamyl chloride for N,N-dimethylsulfamyl chloride. Product was isolated as its dicyclohexylamine salt, mp 172°–174° C.

Me$_2$NSO$_2$-TYR(OMe)

Prepared as above, substituting TYR(OMe) for PHE. Product was isolated as its dicyclohexylamine salt, mp 157°–159° C.

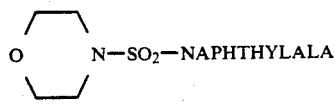

L-1-Naphthylalanine (860 mg) was converted to its tetra-n-butylammonium salt and dissolved in anhydrous THF (25 mL). This solution was treated with morpholinosulfamyl chloride (370 mg) and stirred for 21 hours at room temperature in a stoppered flask. The resulting mixture was partitioned between ethyl acetate and 1N HCl. The organic layer was washed with 0.5 N NaOH and the basic aqueous layer was acidified to pH 2 with concentrated hydrochloric acid. The product was then extracted into a mixture of ethyl acetate and toluene, this solution was dried over magnesium sulfate and the dried solution was evaporated to give a crisp foam (440 mg). 100 MHz NMR (CDCl3) δ 5.4 (broad doublet, SO$_2$NH). Excess naphthylalanine can be recovered for recycling by adjusting the first HCl extract to pH 5.5 and filtration of the resulting precipitate.

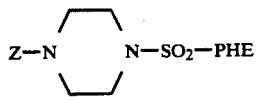

L-Phenylalanine (1.65 g) was converted to its tetramethylammonium salt and dissolved in a mixture of anhydrous THF (50 mL) and anhydrous 2-propanol (12 mL). 4-Carbobenzyloxypiperazinosulfamyl chloride (1.59 g) was added and the reaction was stirred for 16 hours in a stoppered flask. The resulting suspension was evaporated and the residue was partitioned between dichloromethane and 1N HCl. The organic layer was washed with 1N HCl then extracted with 0.3 N NaOH (2×60 mL). The basic extracts were immediately acidified to pH 1 with concentrated HCl and extracted with ethyl acetate. This extract was dried over magnesium sulfate and evaporated to give the desired product as an off-white solid (1.35 g). 200 MHz NMR (CDCl$_3$+DMSO-d$_6$) δ6.2 (broad doublet, SO$_2$NH), 5.0 (S, Ph-CH$_2$-O).

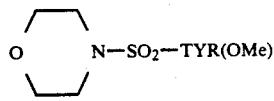

Prepared from the tetramethylammonium salt of TYR(OMe) and morpholinosulfamyl chloride as above. 200 MHz NMR (CDCl$_3$+DMSO-d$_6$) δ6.0 (broad doublet, SO$_2$NH), 3.6 (S, OCH$_3$).

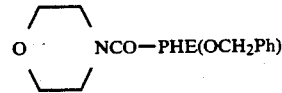

A solution of morpholine (0.87 g), triethylamine (1.4 ml), and diethyl ether (100 ml) was added dropwise to a 17% solution of phosgene in toluene (15 g) at 0°. The mixture was warmed to 25° over one hour and solid removed by filtration. The filtrate was evaporated and redissolved in CH$_2$Cl$_2$ (25 ml). This solution was added to a solution of PHE(OCH$_2$Ph) (2.2 g), triethylamine (1.4 ml), and CH$_2$Cl$_2$ (50 ml). The reaction was kept at 25° for eighteen hours then washed with 0.5 N HCl. The organic layer was dried over MgSO$_4$ and evaporated. The residue was purified by flash chromatography on silica gel (CHCl$_3$) to give a gum which slowly solidifies (3.1 g). TLC R$_f$=0.7 (silica gel, CHCl$_3$-MeOH, 9:1).

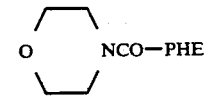

A solution of morpholinocarbamyl-PHE(OCH$_2$Ph) (3.0 g) in THF (100 ml) was treated with 10% Pd/C (0.25 g) under H2 atmosphere (50 psi) for four hours. Catalyst was removed by filtration and the filtrate was evaporated to give a solid (2.3 g). TLC R$_f$=0.1 (silica gel, CHCl$_3$-MeOH, 4:1).

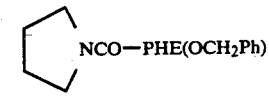

Following the procedure for

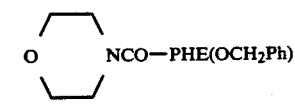

above, pyrrolidine was substituted for morpholine.

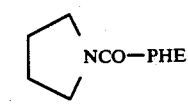

Hydrogenolysis of the benzyl ester above using 10% Pd/C as catalyst, THF as solvent, and 50 psi H₂ atmosphere gives pyrrolidinocarbamyl-PHE.

MORPHOLINOACETIC ACID.HCl

A solution of ethyl bromoacetate (10 ml) in diethyl ether (150 ml) was treated dropwise with morpholine (16 ml). The resulting mixture was stirred two hours at 25°, filtered, and the filtrate was evaporated. The residue was distilled (Kugelrohr, 90°–95°, 1 mm). The distillate (13.5 g) was heated at 90°–95° in 6 N HCl (150 ml) for ninety minutes then evaporated to afford a crystalline mass. Trituration with 2-propanol and drying at 25 mm, 40° gives a colorless, crystalline solid (13 g), mp 169°–171° C.

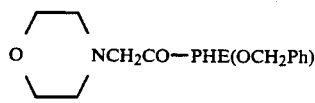

A mixture of morpholinoacetic acid.HCl (1.85 g), DCC (2.1 g), HOBT.H₂O (1.4 g), triethylamine (1.4 ml), and CH₂Cl₂ (100 ml) was stirred for ten minutes at 25° then treated with a solution of PHE(OCH₂Ph) (2.6 g) in CH₂Cl₂ (10 ml). After twenty-four hours at 25° the reaction mixture was filtered and the filtrate was washed with 5% aqueous Na₂CO₃ (75 ml), dried over MgSO₄, and evaporated. The major product was isolated by flash chromatography on silica gel, eluting with CHCl₃-ethyl acetate (98:2). MS (FAB) 383 (m+1).

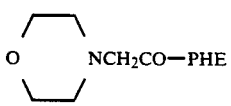

Hydrogenolysis of morpholinoacetyl-PHE(OCH₂Ph) was performed in the same manner as for morpholinocarbamyl-PHE(OCH₂Ph) to give this compound. NMR 5 8.8 (br, 1H), 7.6 (d, 1H), 7.2 (m, 5H), 4.7 (q, 1H), 3.6 (t, 4H), 3.1 (m, 4H), 2.5 (t, 4H).

BOC-LYS(Z)-STA-NHCH₂CH(CH₃)CH₂CH₃

BOC-LYS(Z) (1.98 g), STA-NHCH₂CH(CH₃)CH₂CH₃ (1.3 g), HOBT.H₂O (0.72 g), were mixed together in DMF (15 ml) and cooled to 0°. DCC (1.1 g) was added, and the mixture was allowed to warm slowly to 25° and then stir for 72 hours. The mixture was filtered, and the filtrate was extracted with EtOAc and water. The organic phase was washed with water, sodium bicarbonate solution, and brine. The organic phase was dried over sodium sulfate, filtered, and evaporated. The residue was eluted from silica gel with 1:1 EtOAc/hexane to give 2.7 g of product.

The following compounds are prepared in an analogous manner:

BOC—LYS(Z)—CYSTA—NHCH₂CH(CH₃)CH₂CH₃,

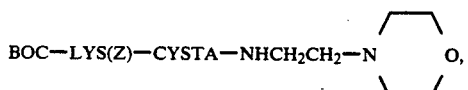

BOC—LYS(Z)—CHSTA—NHCH₂CH(CH₃)CH₂CH₃,

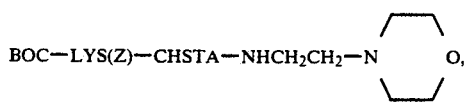

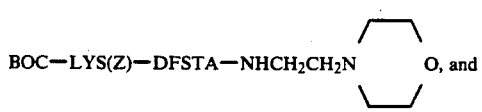

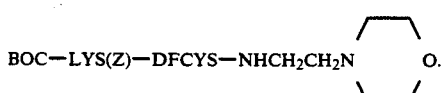

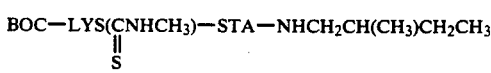

BOC—LYS(CNHCH₃)—STA—NHCH₂CH(CH₃)CH₂CH₃
        ||
        S

A solution of BOC-LYS(Z)-STA-NHCH₂CH(CH₃)CH₂CH₃ (5 1 g) in MeOH (100 ml) was treated with 20% Pd/C (1.0 g) under H2 atmosphere (50 psi) for six hours at 25°. Catalyst was removed by filtration and the filtrate was evaporated to a solid. This solid was dissolved in a mixture of CHCl₃ (40 ml) and THF (80 ml) and treated with methyl isothiocyanate (0.62 g). The resulting solution was stirred at 25° overnight and evaporated. The major product was isolated by flash chromatography on silica gel, eluting with CHCl₃-MeOH (98:2) to afford the desired product (4.1 g). MS (FAB) 546 (m+1).

The following compounds were prepared in an analogous manner:

BOC—LYS(CNHMe)—CYSTA—NHCH₂CH(CH₃)CH₂CH₃,
        ||
        S

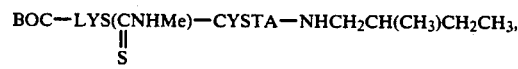

BOC—LYS(CNHMe)—CHSTA—NHCH₂CH(CH₃)CH₂CH₃,
        ||
        S

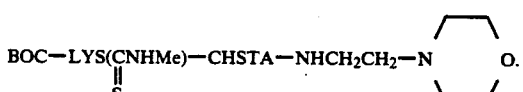

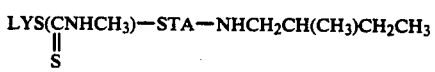

A solution of the above BOC-protected dipeptide (2 g) in CH₂Cl₂ (40 ml) was treated with methanolic HCl (20 ml), stirring at 25° for one hour. The reaction mixture was evaporated and the residue was partitioned between CH2Cl2 (50 ml) and 10% aqueous Na₂CO₃ (25 ml). The organic layer was dried over MgSO₄ and evaporated to a gum. TLC R$_f$=0.1 (silica gel, CHCl₃-MeOH, 9:1).

The following compounds are prepared in an analogous manner:

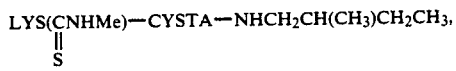
LYS(CNHMe)—CYSTA—NHCH2CH(CH3)CH2CH3,
‖
S

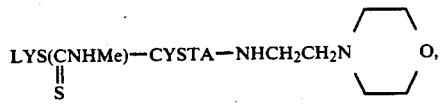
LYS(CNHMe)—CYSTA—NHCH2CH2N◯O,
‖
S

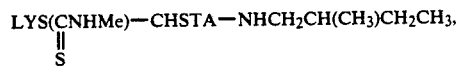
LYS(CNHMe)—CHSTA—NHCH2CH(CH3)CH2CH3,
‖
S

LYS(CNHMe)—CHSTA—NHCH2CH2—N◯O,
‖
S

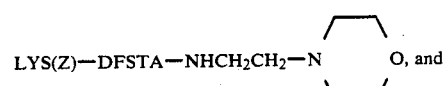
LYS(Z)—DFSTA—NHCH2CH2—N◯O, and

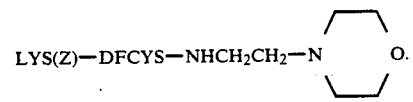
LYS(Z)—DFCYS—NHCH2CH2—N◯O.

HIS(TR)-STA-NHCH2CH(CH3)CH2CH3

A solution of Z-HIS(TR)-STA-NHCH2CH(CH3)CH2CH3 (5.4 g) in MeOH (200 ml) was treated with 20% Pd/C (0.5 g) under H2 atmosphere (50 psi) at 25°. After five hours the catalyst was removed by filtration and the filtrate was evaporated to give a gum (4.4 g). TLC $R_f$=0.2 (silica gel, CHCl3-MeOH, 9:1).

The following compounds are prepared in an analogous manner:

HIS(TR)—CYSTA—NHCH2CH(CH3)CH2CH3,

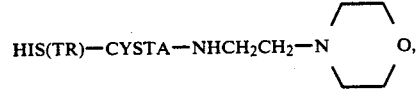
HIS(TR)—CYSTA—NHCH2CH2—N◯O,

HIS(TR)—CHSTA—NHCH2CH(CH3)CH2CH3, and

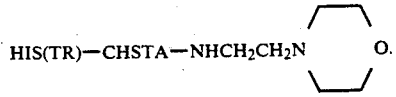
HIS(TR)—CHSTA—NHCH2CH2N◯O.

H2NCH(CO2Me)CO2CH2Ph

Methyl, benzyl isonitroso malonate was prepared from methyl, benzyl malonate (obtained from Aldrich Chemical Corp.) by the procedure described in *Organic Synthesis*, Col. Vol. V, p. 373. The crude product thus obtained was reduced to the title compound by the procedure described in the *Journal of the American Chemical Society*, Vol. 75, p. 1970, Apr. 20, 1953. Crude product was used without further purification or analyses in the following step.

BOC-NHCH(CO2Me)CO2CH2Ph

H2NCH(CO2Me)CO2CH2Ph (94 g) was dissolved in ethyl ether (750 ml) and cooled to 5°. Di-t-butyldicarbonate (91.7 g) was added and the mixture was held at 4° overnight. The mixture was stripped to an orange oil (135 g). This oil was chromatographed on silica gel, eluting with hexane-ethyl acetate (85:15). The major product was recovered as an oil which solidified upon standing (67 g). MS (FAB) 324 (m+1).

BOC-NHCH(CO2Me)CO2H

BOC-NHCH(CO2Me)CO2CH2Ph (16.2 g) was dissolved in MeOH (250 ml), to which was added 20% Pd/C (0.66 g). The suspension was purged with H2 for 1.5 hours, filtered, and stripped at 30° in vacuo, giving a syrup (12.5 g) which was kept at 4° until use in the following step.

BOC-NHCH(CO2Me)CO-STA-NHCH2CH(CH3)CH2CH3

BOC-NHCH(CO2Me)CO2H (12.5 g) was dissolved in CH2Cl2 (340 ml) and cooled to −3°. A solution of HOBT.H2O (7.0 g) in DMF (15 ml) was added, followed by a cold solution of DCC (10.6 g) in CH2Cl2 (50 ml). A cold solution of STA-NHCH2CH(CH3)CH2CH3 (11.3 g) in CH2Cl2 (60 ml) was then added and the mixture was stored at 4° overnight. The mixture was filtered and the filtrate was washed consecutively with 1 N citric acid, brine, saturated aqueous NaHCO3, and brine. The organic phase was dried over MgSO4 and stripped to a glass (23.3 g). Chromatography on silica gel, eluting with CHCl3-MeOH (98:2) gives the purified product as a foam (13.9 g). MS (FAB) 460 (m+1).

The following compounds were prepared in an analogous manner:

BOC—NHCH(CO2Me)CO—CYSTA—NHCH2CH(CH3)CH2CH3,

BOC—NHCH(CO2Me)CO—CYSTA—NHCH2CH2—N◯O,

BOC—NHCH(CO2Et)CO—CHSTA—NHCH2CH(CH3)CH2CH3,

BOC—NHCH(CO2Me)CO—CHSTA—NHCH2CH2—N◯O,

BOC—NHCH(CO2Me)CO—DFSTA—NHCH2CH2—NO,

BOC—NHCH(CO2Me)CO—DFCYS—NHCH2CH(CH3)CH2CH3,

BOC—NHCH(CO2Me)CO—DFCYS—NHCH2CH2N(CH2CH2OH)2, and

BOC—NHCH(CO2Me)CO—DFCYS—NHCH2CH2—NO.

H2NCH(CO2Me)CO-STA-NHCH2CH(CH3)CH2CH3

BOC-NHCH(CO2Me)CO-STA-NHCH2CH(CH3)CH2CH3 (16 6 g) was dissolved in CH2Cl2 (300 ml), to which was added trifluoroacetic acid (50 ml). After stirring two hours, the mixture was stripped to a syrup which was taken up in ethyl ether-ethyl acetate (1:1). This solution was charged with saturated aqueous NaHCO3 (50 ml), followed by agitation. Additional solid NaHCO3 was added until the mixture became saturated. The organic phase was washed with brine, dried over MgSO4 and stripped to a yellow foam (10.5 g) which was suitable for use in subsequent steps (Example 8) without further purification. MS (FAB) 360 (m+1).

The following compounds are prepared in an analogous manner:

H2NCH(CO2Me)CO—CYSTA—NHCH2CH(CH3)CH2CH3,

H2NCH(CO2Me)CO—CYSTA—NHCH2CH2—N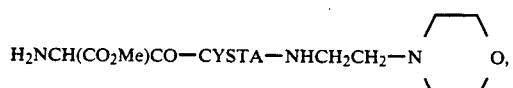O,

H2NCH(CO2Et)CO—CHSTA—NHCH2CH(CH3)CH2CH3,

H2NCH(CO2Me)CO—CHSTA—NHCH2CH2—N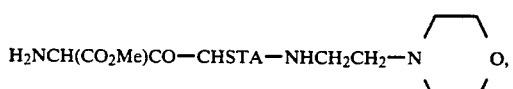O,

H2NCH(CO2Me)CO—DFSTA—NHCH2CH2—N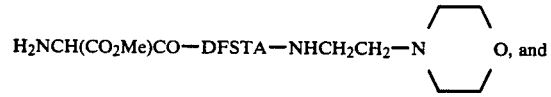O, and

H2NCH(CO2Me)CO—DFCYS—NHCH2CH2—N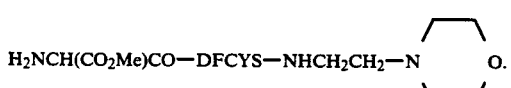O.

BOC-ALG-STA-NHCH2CH(CH3)CH2CH3

A mixture of BOC-ALG (1.76 g), HOBT.H2O (1.16 g) and DMF (20 mL) was stirred in an ice bath and treated with STA-NHCH2CH(CH3)CH2CH3 (2.0 G) and DCC (1.79 g). The mixture was stirred in an ice bath for 3 hours and then overnight at room temperature. After filtering, the filtrate was concentrated under high vacuum. The residue was taken up in EtOAc and washed with 1N citric acid, brine, saturated NaHCO3, and brine. After drying over Na2SO4, the solution was concentrated to yield an orange solid which was purified by flash chromatography (MeOH/CHCl3 2:98) to yield BOC-ALG-STA-NHCH2CH(CH3)CH2CH3 (2.1 g) as a white foam. MS (FAB) 442 (m+1).

The following compounds were obtained in an analogous manner:

BOC—ALG—CYSTA—NHCH2CH(CH3)CH2CH3,

BOC—ALG—CHSTA—NHCH2CH(CH3)CH2CH3,

BOC—ALG—CYSTA—NHCH2CH2—N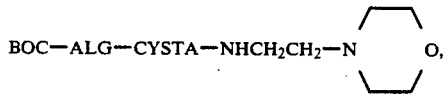O,

BOC—MET—CHSTA—NHCH2CH(CH3)CH2CH3,

BOC—ALG—CHSTA—NHCH2CH2—N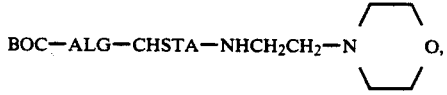O,

BOC—ALG—DFSTA—NHCH2CH2—N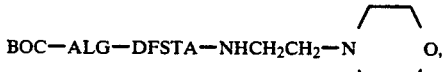O,

BOC—ALG—DFCYS—NHCH2CH(CH3)CH2CH3, and

BOC—ALG—DFCYS—NHCH2CH2N(CH2CH2OH)2.

BOC-ALG

ALG was prepared according to the procedure described in the *Journal of the American Chemical Society*, Vol. 109, pp. 4649–4659, 1987. A solution of ALG (16 g) in a mixture of dioxane (150 mL) and 2N NaOH (70 mL) was treated with di-t-butyldicarbonate (34 g). The mixture was stirred overnight, basified to pH=8.5 with 2N NaOH, diluted with water and extracted with ether. The aqueous solution was acidified with citric acid and extracted twice with ether. The combined ether extracts were washed with brine, dried over Na2SO4 and concentrated to yield BOC-ALG as a solid. MS (CI, CH4) 216 (m+1).

We claim:

1. A compound selected from the group consisting of:

Me2NSO2—PHE,
Me2NSO2—TYR(OMe),

-continued
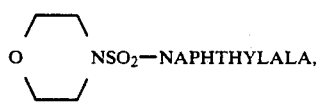
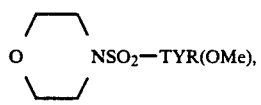
-continued
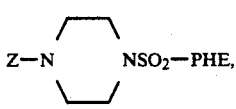
wherein 2 is selected from the group consisting of h and CH₃; and the dicyclohexylamine salts thereof.
* * * * *

UNITED STATES PATENT AND TRADEMARK OFFICE
CERTIFICATE OF CORRECTION

PATENT NO. : 5,162,527
DATED : 11/10/92
INVENTOR(S) : Annette M. Doherty, et al

It is certified that error appears in the above-identified patent and that said Letters Patent is hereby corrected as shown below:

Column 86, line 16, delete the "2" following "wherein" and insert instead --Z--.

column 86, line 16, delete the "h" following "consisting of" and instead --H--.

Signed and Sealed this

Thirtieth Day of November, 1993

Attest:

BRUCE LEHMAN

Attesting Officer

Commissioner of Patents and Trademarks